United States Patent
Puzio et al.

(10) Patent No.: US 7,537,421 B2
(45) Date of Patent: May 26, 2009

(54) DEAD SPINDLE PTO WITH COMPLIANT GROUNDING MECHANISM

(75) Inventors: Daniel Puzio, Baltimore, MD (US); Stephen A. Debelius, New Freedom, PA (US)

(73) Assignee: Black & Decker Inc., Newark, DE (US)

( * ) Notice: Subject to any disclaimer, the term of this patent is extended or adjusted under 35 U.S.C. 154(b) by 61 days.

(21) Appl. No.: 11/693,274

(22) Filed: Mar. 29, 2007

(65) Prior Publication Data

US 2007/0170665 A1 Jul. 26, 2007

Related U.S. Application Data

(63) Continuation-in-part of application No. 11/227,200, filed on Sep. 16, 2005, and a continuation-in-part of application No. 11/400,378, filed on Apr. 10, 2006.

(60) Provisional application No. 60/787,154, filed on Mar. 30, 2006.

(51) Int. Cl.
*B23B 31/16* (2006.01)

(52) U.S. Cl. .................. 408/124; 408/139; 279/60; 279/135; 279/902

(58) Field of Classification Search ................. 408/124, 408/139; 279/60–65, 134, 135, 902; *B23B 31/16*
See application file for complete search history.

(56) References Cited

U.S. PATENT DOCUMENTS

| | | |
|---|---|---|
| 913,059 A | 2/1909 | Savage |
| 1,705,275 A * | 3/1929 | Von Neudeck ............... 279/64 |
| 2,353,514 A | 7/1944 | Slater |
| 2,684,856 A | 7/1954 | Stoner |
| 2,716,555 A | 8/1955 | Walker |
| 2,848,911 A | 8/1958 | Black |
| 2,931,660 A | 4/1960 | Barwinkel |
| 2,963,913 A * | 12/1960 | Wensloff ................. 74/15.6 |
| 3,506,277 A | 4/1970 | Harms |
| 3,545,766 A | 12/1970 | Osborn |
| 3,776,647 A | 12/1973 | Hart |
| 3,970,323 A | 7/1976 | Schnizler, Jr. |
| 4,085,337 A * | 4/1978 | Moeller ................. 307/115 |
| 4,094,523 A | 6/1978 | Derbyshire |
| 4,260,169 A | 4/1981 | Hall |
| 4,277,074 A | 7/1981 | Kilberis |
| 4,302,021 A | 11/1981 | Röhm |
| 4,317,578 A | 3/1982 | Welch |
| 4,323,324 A | 4/1982 | Eberhardt |

(Continued)

FOREIGN PATENT DOCUMENTS

DE 1985830 5/1968

(Continued)

*Primary Examiner*—David P Bryant
*Assistant Examiner*—Eric A. Gates
(74) *Attorney, Agent, or Firm*—Capitol City TechLaw

(57) ABSTRACT

A power driver may include a housing, a tool chuck and a power take off mechanism. The tool chuck may have an input shaft mounted for rotation on the housing. The input shaft may support jaws. A chuck actuating shaft may be mounted for rotation on the input shaft. The power take off mechanism may be connected to the tool chuck. The power take off mechanism may be adjustable into a DRILL DRIVE MODE to rotationally drive the input shaft and the chuck actuating shaft together as a unit, and a CHUCK MODE to rotationally drive the chuck actuating shaft relative to the input shaft. The power take off mechanism may include a shift ring that is movable axially to achieve the various operational modes. During such axial movement, the shift ring may be rotationally locked to the housing and/or transmission components via compliant grounding mechanisms.

20 Claims, 17 Drawing Sheets

U.S. PATENT DOCUMENTS

| | | | |
|---|---|---|---|
| 4,358,230 A | 11/1982 | Rohlin |
| 4,395,170 A | 7/1983 | Clarey |
| 4,493,407 A | 1/1985 | Newton |
| 4,498,682 A | 2/1985 | Glore |
| 4,526,497 A | 7/1985 | Hatfield |
| 4,527,809 A | 7/1985 | Umbert |
| 4,536,113 A | 8/1985 | Hatfield |
| 4,557,703 A | 12/1985 | Rivin |
| 4,605,345 A | 8/1986 | Giughese |
| 4,628,918 A | 12/1986 | Johnson, Jr. |
| 4,655,464 A | 4/1987 | Manschitz et al. |
| 4,664,394 A | 5/1987 | Theissig et al. |
| 4,669,930 A | 6/1987 | Stenmark |
| 4,669,932 A | 6/1987 | Hartley |
| 4,682,918 A | 7/1987 | Palm |
| 4,788,021 A | 11/1988 | Griffiths |
| 4,802,798 A | 2/1989 | Adamson |
| 4,824,298 A | 4/1989 | Lippacher et al. |
| 4,840,387 A | 6/1989 | McCarthy |
| 4,848,779 A | 7/1989 | Wheeler et al. |
| 4,930,793 A | 6/1990 | Ando |
| 4,951,955 A | 8/1990 | Sakamaki |
| 4,955,623 A | 9/1990 | Röhm |
| 4,958,840 A | 9/1990 | Palm |
| 4,976,575 A | 12/1990 | Kappelhof et al. |
| 4,998,589 A | 3/1991 | Wiesendanger |
| 5,011,343 A | 4/1991 | Saban et al. |
| 5,019,023 A | 5/1991 | Kurosawa |
| 5,022,278 A | 6/1991 | DeCaussin |
| 5,031,925 A * | 7/1991 | Tatsu et al. ............. 279/64 |
| 5,067,376 A | 11/1991 | Fossella |
| 5,090,273 A | 2/1992 | Fossella |
| 5,125,673 A | 6/1992 | Huff et al. |
| 5,145,193 A | 9/1992 | Röhm |
| 5,147,164 A | 9/1992 | Fraver |
| 5,171,030 A | 12/1992 | Röhm |
| 5,172,923 A | 12/1992 | Nakamura |
| 5,174,588 A | 12/1992 | Reibetanz et al. |
| 5,183,274 A | 2/1993 | Sakamaki |
| 5,195,760 A * | 3/1993 | Wheeler et al. ............. 279/60 |
| 5,197,749 A | 3/1993 | Moore et al. |
| 5,215,317 A | 6/1993 | Jordan et al. |
| 5,232,230 A | 8/1993 | Lin |
| 5,286,041 A | 2/1994 | Röhm |
| 5,299,814 A | 4/1994 | Salpaka |
| 5,322,303 A | 6/1994 | Nakamura |
| 5,339,908 A | 8/1994 | Yokota et al. |
| 5,340,248 A | 8/1994 | Enbergs |
| 5,342,154 A | 8/1994 | Holzer |
| 5,343,961 A | 9/1994 | Ichikawa |
| 5,348,317 A | 9/1994 | Steadings et al. |
| 5,348,318 A | 9/1994 | Steadings et al. |
| 5,407,215 A | 4/1995 | Yang |
| 5,419,663 A | 5/1995 | Psomas |
| 5,431,420 A | 7/1995 | Huff et al. |
| 5,435,578 A | 7/1995 | Röhm |
| 5,448,931 A | 9/1995 | Fossella et al. |
| 5,458,345 A | 10/1995 | Amyot |
| 5,499,829 A | 3/1996 | Röhm |
| 5,499,830 A | 3/1996 | Schnizler |
| 5,531,549 A | 7/1996 | Fossella |
| 5,553,873 A | 9/1996 | Salpaka et al. |
| 5,573,358 A | 11/1996 | Gobbers et al. |
| 5,624,125 A | 4/1997 | Röhm |
| 5,685,549 A | 11/1997 | Yang |
| 5,732,956 A | 3/1998 | Huff et al. |
| 5,741,016 A | 4/1998 | Barton et al. |
| 5,795,110 A | 8/1998 | Wirth et al. |
| 5,820,134 A | 10/1998 | Subils Valls |
| 5,908,076 A | 6/1999 | Marcengill et al. |
| 5,918,685 A | 7/1999 | Ulbrich et al. |
| 5,922,538 A | 7/1999 | Hazel et al. |
| 5,951,026 A | 9/1999 | Harman, Jr. et al. |
| 5,957,469 A | 9/1999 | Miles et al. |
| 5,988,653 A | 11/1999 | Kuo |
| 5,988,958 A | 11/1999 | Mack |
| 5,992,859 A | 11/1999 | Lin |
| 6,007,071 A | 12/1999 | Middleton |
| 6,007,277 A | 12/1999 | Olson et al. |
| 6,017,039 A | 1/2000 | Gaddis et al. |
| 6,056,298 A | 5/2000 | Williams |
| 6,079,716 A | 6/2000 | Harman, Jr. et al. |
| 6,105,450 A | 8/2000 | Sasaki et al. |
| 6,139,228 A | 10/2000 | Longo |
| 6,173,972 B1 | 1/2001 | Temple-Wilson et al. |
| 6,241,260 B1 * | 6/2001 | Judge et al. ............. 279/64 |
| 6,260,856 B1 | 7/2001 | Temple-Wilson |
| 6,354,605 B1 | 3/2002 | Aultman |
| 6,398,226 B1 | 6/2002 | Huggins et al. |
| 6,431,289 B1 | 8/2002 | Potter |
| 6,488,286 B2 | 12/2002 | Yaksich |
| 6,488,287 B2 | 12/2002 | Gaddis et al. |
| 6,506,002 B1 | 1/2003 | Cummins |
| 6,517,295 B2 | 2/2003 | Lin |
| 6,523,658 B2 | 2/2003 | Furuta et al. |
| 6,648,563 B2 | 11/2003 | Rohm |
| 6,729,812 B2 | 5/2004 | Yaksich et al. |
| 6,733,393 B2 | 5/2004 | Rivin |
| 6,736,410 B2 | 5/2004 | Barton et al. |
| 6,832,764 B2 | 12/2004 | Steadings et al. |
| 6,843,484 B2 * | 1/2005 | Schroeder ............. 279/60 |
| 7,021,400 B2 | 4/2006 | Oretti |
| 7,073,606 B2 | 7/2006 | Mamber et al. |
| 7,328,904 B2 * | 2/2008 | Schell et al. ............. 279/60 |
| 2001/0026051 A1 | 10/2001 | Gifford et al. |
| 2003/0077137 A1 | 4/2003 | Rohm |
| 2004/0146367 A1 | 7/2004 | Gerhardt et al. |
| 2005/0013674 A1 | 1/2005 | Vidal |
| 2006/0027978 A1 | 2/2006 | Young et al. |
| 2006/0066063 A1 | 3/2006 | Nickels et al. |
| 2006/0188350 A1 * | 8/2006 | Gehret et al. ............. 408/240 |

FOREIGN PATENT DOCUMENTS

| | | |
|---|---|---|
| DE | 2317779 | 10/1974 |
| DE | 7536582 | 5/1976 |
| DE | 7617128 | 12/1976 |
| DE | 2757140 | 6/1979 |
| DE | 8002633 | 7/1980 |
| DE | 3110458 | 10/1982 |
| DE | 3140776 | 4/1983 |
| DE | 8513848 | 8/1985 |
| DE | 9006555 | 9/1990 |
| DE | 9405628 | 7/1994 |
| DE | 3527234 | 2/1997 |
| DE | 29820433 | 3/1999 |
| DE | 29913083 | 10/1999 |
| DE | 10125186 | 12/2002 |
| DE | 202004003323 | 8/2004 |
| DE | 10359420 | 7/2005 |
| EP | 0448801 | 10/1991 |
| EP | 0515371 | 12/1992 |
| EP | 0620069 | 10/1994 |
| EP | 0716896 | 1/1995 |
| EP | 0674961 | 10/1995 |
| EP | 1101553 | 5/2001 |
| FR | 1602481 | 1/1971 |
| WO | WO 00/35619 | 6/2000 |
| WO | WO 02/058893 A1 | 8/2002 |
| WO | WO 2005/025792 | 3/2005 |
| WO | WO 2006/034287 A2 | 3/2006 |

* cited by examiner

DEAD SPINDLE PTO WITH COMPLIANT GROUNDING MECHANISM

CROSS REFERENCE TO RELATED APPLICATIONS

This U.S. non-provisional application claims priority under 35 USC §119 to U.S. Provisional Application No. 60/787,154 filed Mar. 30, 2006, the content of which is incorporated herein in its entirety by reference. This U.S. non-provisional application is a Continuation-In-Part of (1) U.S. application Ser. No. 11/227,200 filed Sep. 16, 2005 and (2) U.S. application Ser. No. 11/400,378 filed Apr. 10, 2006, the content of both of which is incorporated herein in its entirety by reference.

BACKGROUND

1. Field of the Invention

Example embodiments of the present invention relate in general to tool chucks for attachment of accessories to power drivers, and more particularly to a tool chuck having chuck jaws that may be actuated via power from the driver's transmission.

2. description of Related Art

A tool chuck may be provided on a power driver for holding an accessory. The tool chuck may be actuated (to open and close the chuck jaws) via a power take off ("PTO") feature. Numerous and varied PTO features are described in commonly-assigned, copending application Ser. Nos. 11/227,200 filed Sep. 16, 2005, and 11/400,378 filed Apr. 10, 2006. In those copending applications, a shift ring of the PTO mechanism may be axially positioned to achieve different operational modes inclusive of a MANUAL OVERRIDE MODE, a DRILL/DRIVE MODE and a CHUCK MODE. When positioned in the CHUCK MODE, the shift ring may be positioned to engage with corresponding features on the driver housing, to thereby rotationally lock the shift ring to the driver housing.

SUMMARY

According to an example, non-limiting embodiment, a power driver may include a housing. A lock member may be mounted for axial movement on the housing. The lock member may be rotationally fixed to the housing. A tool chuck may be mounted for rotation on the housing. The tool chuck may support jaws. A shift member may be provided for axial movement relative to the tool chuck between (1) a first position in which the shift member may be rotatable relative to the lock member to achieve a DRILL/DRIVE MODE to rotationally drive the jaws, and (2) a second position in which the shift member may rotationally lock with the lock member if the shift member is clocked to the lock member to achieve a CHUCK MODE to open or close the jaws. The lock member may be axially displaced by the shift member when the shift member is moved to the second position and the shift member is not clocked to the lock member.

According to another example, non-limiting embodiment, a power driver may include a housing. A lock member may be mounted for axial movement on the housing. The lock member may be rotationally fixed to the housing. A tool chuck may have an input shaft, and a chuck actuating shaft may be mounted for rotation on the input shaft. A power take off mechanism may be connected to the tool chuck. The power take off mechanism may include a shift member for axial movement between (1) a first position in which the shift member may be rotatable relative to the lock member to achieve a DRILL/DRIVE MODE to rotationally drive the input shaft and the chuck actuating shaft together as a unit, and (2) a second position in which the shift member may rotationally lock with the lock member if the shift member is clocked to the lock member to achieve a CHUCK MODE to rotationally drive the chuck actuating shaft relative to the input shaft. The lock member may be axially displaced by the shift member when the shift member is moved to the second position and the shift member is not clocked to the lock member.

According to another example, non-limiting embodiment, a power driver may include a housing. A lock member may be mounted for axial movement on the housing. The lock member may be rotationally fixed to the housing. A transmission output may be provided. A tool chuck may have an input shaft mounted for rotation on the housing and supporting jaws, and a chuck actuating shaft may be mounted for rotation on the input shaft. An output coupling may be rotationally fixed to the input shaft. A power take off drive disk may be rotationally fixed to the chuck actuating shaft. A shift member may be mounted for axial movement between (1) a first position in which the shift member may rotationally lock the output coupling to the transmission output, and (2) a second position in which the shift member may rotationally lock the output coupling to the lock member if the shift member is clocked to the lock member. The lock member may be axially displaced by the shift member when the shift member is moved to the second position and the shift member is not clocked to the lock member.

The above and other features of the invention including various and novel details of construction and combinations of parts will now be more particularly described with reference to the accompanying drawings. It will be understood that the details of the example embodiments are shown by way of illustration only and not as limitations of the invention. The principles and features of this invention may be employed in varied and numerous embodiments without departing from the spirit and scope of the invention.

DESCRIPTION OF EXAMPLE, NON-LIMITING EMBODIMENTS

I. Example Embodiment Depicted in FIGS. 1-7

Figure 1:
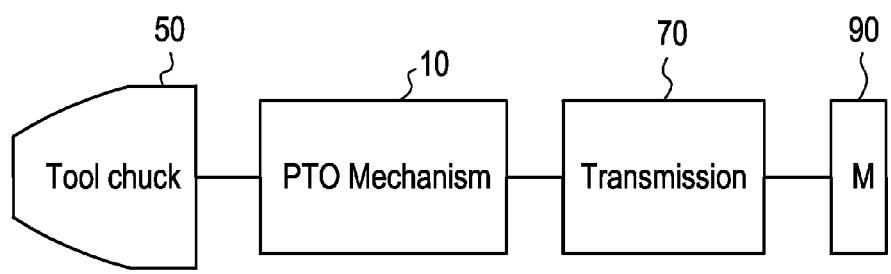
FIG. 1 is a schematic illustration of a tool chuck with a power take off mechanism according to an example, non-limiting embodiment.

FIG. 1 schematically shows an example, non-limiting embodiment of a tool chuck 50 that may be provided on a power driver (e.g., a drill) for holding an accessory (e.g., a drill bit). It will be appreciated, however, that the tool chuck 50 may be suitably implemented on a variety of power drivers (other than drills) for holding a variety of accessories (other than drill bits).

The tool chuck 50 may be connected to the transmission 70 of a power driver via a power take off ("PTO") mechanism 10. The transmission 70 may be coupled to an electric motor 90. The transmission 70 may use gearing to effect a change in the ratio between an input rpm (from the electric motor 90) and an output rpm (delivered to the tool chuck 50).

In this example embodiment, the transmission 70 may include three planetary reduction systems. It will be appreciated, however, that the invention is not limited in this regard. For example, more or less than three planetary reduction systems may be implemented. Further, transmissions other than planetary reduction system transmissions (e.g., conventional parallel axis transmissions) may be suitably implemented. Planetary reduction transmissions are well known in this art, and therefore a detailed discussion of the same is omitted. The PTO mechanism 10 may be provided at the output of the transmission 70.

Figure 2:
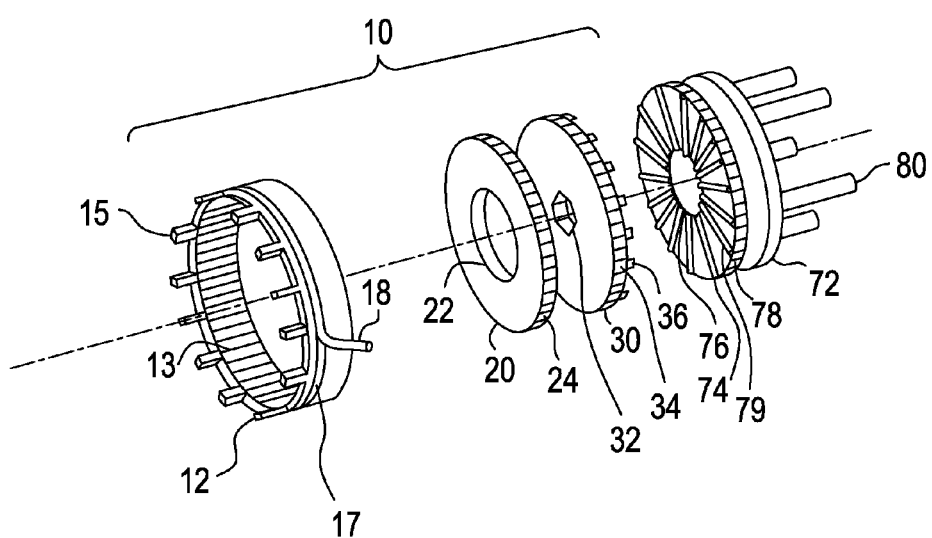
FIG. 2 is an exploded perspective view of the power take off mechanism of FIG. 1.

A. The Structure:

FIG. 2 is an exploded perspective view of the PTO mechanism 10. In this example embodiment, the PTO mechanism 10 may include a shift ring 12, an output coupling 20 and a PTO drive disk 30.

The shift ring 12 may have a radial inward facing surface provided with splines 13 (for selectively engaging with the output coupling 20, the PTO drive disk 30 and a disk 74 of the third stage carrier 72). The shift ring 12 may have lugs 15 extended in an axial forward direction. The lugs 15 may selectively engage with a housing of the driver, not shown. The shift ring 12 may have a continuous circumferential groove 17 for accommodating a wire 18.

The wire 18, which may be slidable through the circumferential groove 17, may have free ends that extend in a radial direction and out of the circumferential groove 17. The fee ends of the wire 18 (serving as cam followers) may be received in a slot of a shift collar (not shown in FIG. 2) rotatably mounted on the driver housing. Upon rotating the shift collar, the slot may influence the cam followers (and thus the shift ring 12) to the desired axial positions, as will be discussed in more detail below.

The output coupling 20 may include a central aperture 22 having a shape that corresponds to the shape of an input shaft 60 (not shown in FIG. 2), discussed in more detail below. The output coupling 20 may have a radial outward facing surface provided with splines 24 that selectively cooperate with the radial inward facing splines 13 of the shift ring 12.

The PTO drive disk 30 may include a central aperture 32 having a shape that corresponds to the shape of a PTO actuator shaft (not shown in FIG. 2), discussed in more detail below. The PTO drive disk 30 may have a radial outward facing surface provided with splines 34 that selectively cooperate with the radial inward facing splines 13 of the shift ring 12. The PTO drive disk 30 may have an axial rearward facing surface provided with clutch features 36. In this example embodiment, the clutch features 36 may be in the form of elongated projections that extend in a radial fashion across the axial rearward facing surface of the PTO drive disk 30.

The disk 74 of the third stage carrier 72 may include a central aperture 76 that extends axially through the third stage carrier 72. The disk 74 may have a radial outward facing surface provided with splines 78 that selectively cooperate with the radial inward facing splines 13 of the shift ring 12. The disk 74 may also include an axial forward facing surface provided with clutch features 79. In this example embodiment, the clutch features 79 may be in the form of elongated projections that extend in a radial fashion across the axial forward facing surface of the disk 74. The clutch features 79 of the disk 74 may cooperate with the clutch features 36 of the PTO drive disk 30. As is well known in this art, the third stage carrier 72 may include shafts 80 that rotatably support planetary gears (not shown).

Figure 3:
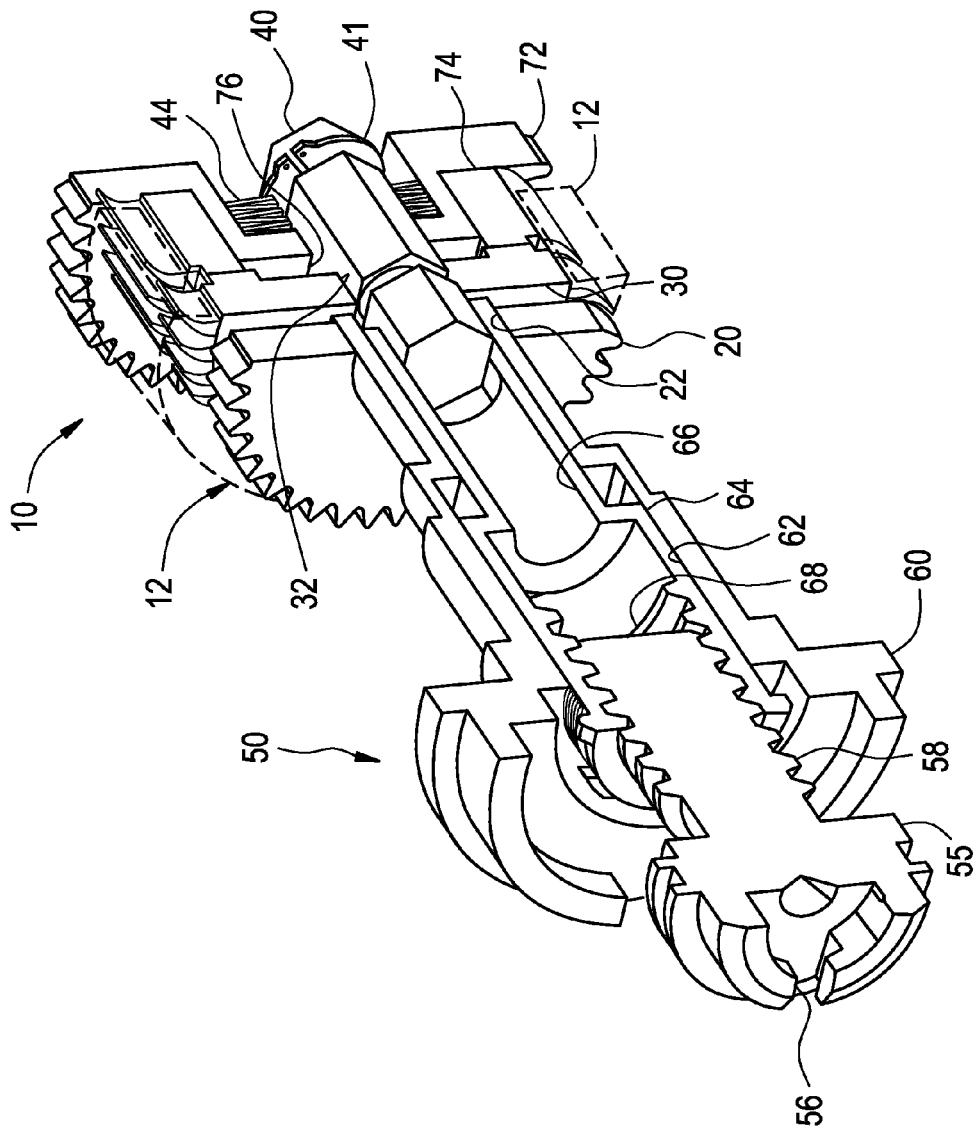
FIG. 3 is a sectional perspective view of the tool chuck mounted on the power take off mechanism of FIG. 1.

FIG. 3 is a sectional perspective view of the PTO mechanism 10 assembled together with the tool chuck 50. Here, the shift ring 12 is shown in phantom for clarity.

The tool chuck 50 may include an input shaft 60. A forward end of the input shaft 60 may support a nose portion (not shown) that may include passageways through which chuck jaws (not shown) are respectively slidable. The passageways of the nose portion may rotationally fix the input shaft 60 to the chuck jaws. The input shaft 60 may have a rear end that extends through the central aperture 22 of the output coupling 20. The rear end of the input shaft 60 may have a radial outward facing surface provided with features that cooperate with corresponding features provided on the radial inward facing surface defining the central aperture 22 so that the input shaft 60 may be rotationally locked to the output coupling 20. Such features are well known in this art. By way of example only, the input shaft 60 may be provided with flats against which flats of the central aperture 22 may abut to rotationally lock together the input shaft 60 and the output coupling 20. The input shaft 60 may include a through bore 62. The through bore 62 may rotatably support a chuck actuating shaft 64.

The chuck actuating shaft 64 may include a through bore 66. The through bore 66 may have a rear end receiving a PTO actuator shaft 40. The rear end of the through bore 66 and the PTO actuator shaft 40 may have corresponding shapes to rotationally fix the chuck actuating shaft 64 to the PTO actuator shaft 40. The forward end of the through bore 66 may be provided with radial inward facing threads 68 that may interact with radial outward facing threads 58 of a chuck actuating screw 55. That is, the chuck actuating shaft 64 may be screw coupled to the chuck actuating screw 55.

The chuck actuating screw 55 may include radial passageways 56 through which the chuck jaws are respectively slidable. The radial passageways 56 may rotationally fix the chuck actuating screw 55 to the chuck jaws. The interaction between the threads 58 and 68 may cause the chuck actuating screw 55 to advance and retract in the axial direction relative to the input shaft 60. It will be appreciated that the chuck actuating screw 55 and input shaft 60 may be rotationally locked together via the chuck jaws.

The PTO actuator shaft 40 may extend through the through bore 66 of the chuck actuating shaft 64, the central aperture 32 of the PTO drive disk 30 and the central aperture 76 of the disk 74. A keeper 41 (in the form of a snap ring, for example) may be mounted on the PTO actuator shaft 40. A spring 44 may be mounted on the PTO actuator shaft 40 and compressed between the third stage carrier 72 and the keeper 41. The PTO actuator shaft 40 may support another keeper (not shown for clarity) via a slot located axially forward of the PTO drive disk 30. As noted above, the PTO actuator shaft 40 may have a shape that corresponds to the shape of the central aperture 32 of the PTO drive disk 30. In this way, the PTO actuator shaft 40 may be rotationally fixed to the PTO drive disk 30.

As shown in FIG. 3, the output coupling 20, the PTO drive disk 30 and the disk 74 of the third stage carrier 72 may be assembled together in a coaxial fashion. Here, the clutch features 36 of the PTO drive disk 30 may face (and engage with) the clutch features 79 of the disk 74. Also, the shift ring 12 (shown in phantom) may be mounted for axial movement so that the radial inward facing splines 13 of the shift ring 12 may selectively engage with the radial outward facing splines 24 of the output coupling 20, the radial outward facing splines 34 of the PTO drive disk 30 and the radial outward facing splines 78 of the disk 74.

Figure 4:
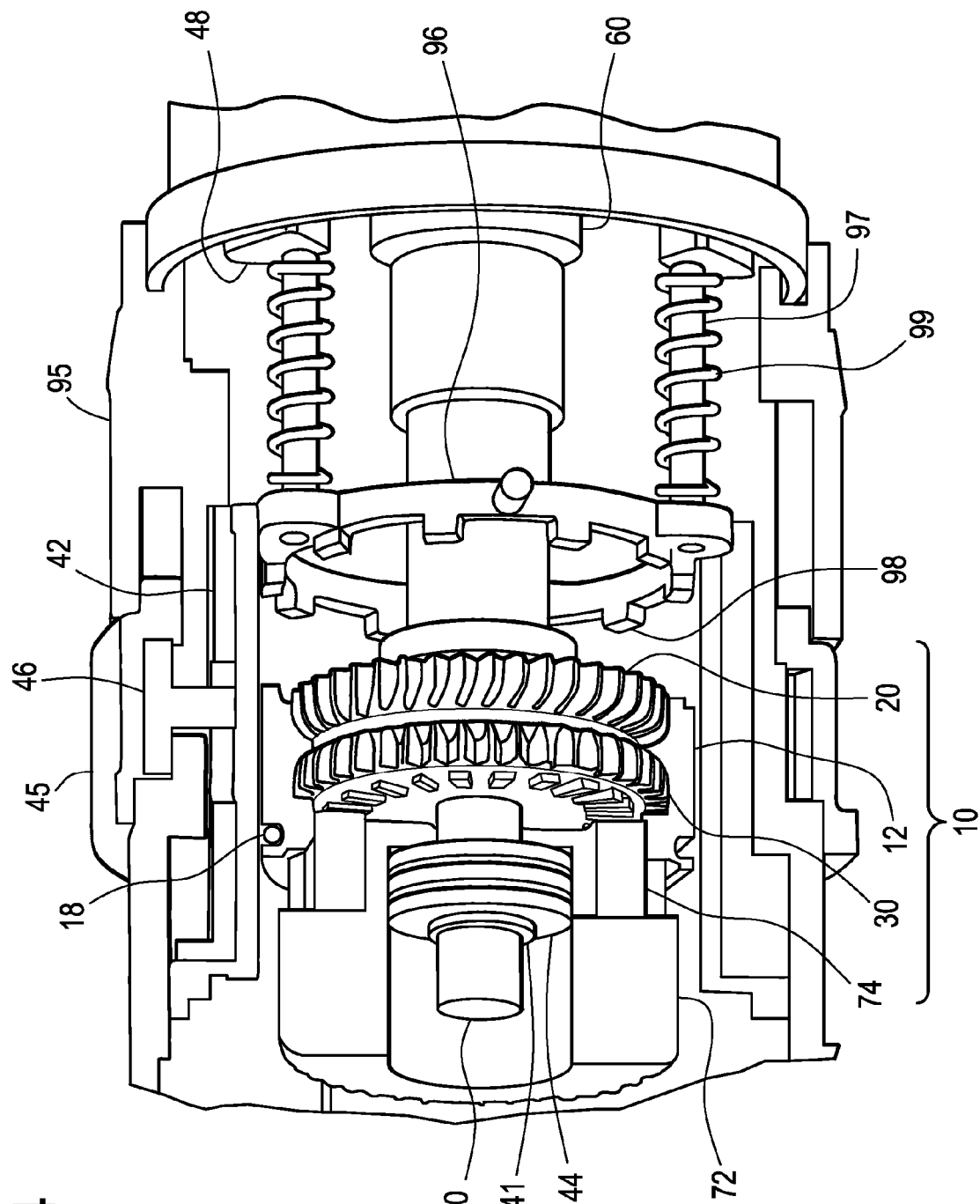
FIG. 4 is a sectional view of the power take off mechanism in a DRILL/DRIVE MODE.

FIG. 4 illustrates the PTO mechanism 10 implemented in an example housing 95 of a power driver. The driver housing 95 may support a mode ring 45 and a shift collar 42, which may be manipulated by a user to axially position the shift ring 12 depicted in FIGS. 2 and 3 to achieve various operational modes.

The mode ring 45 and the shift collar 42 may be mounted for rotation on the driver housing 95. The mode ring 45 and the shift collar 42 may be rotationally fixed together via a radial extension 46. Thus, the mode ring 45 and the shift collar 42 may be rotatable together relative to the driver housing 95.

The shift collar 42 may include a slot (not shown) that extends in a circumferential direction around the shift collar 42. In this example embodiment, the shift collar 42 may include two circumferential slots. The driver housing 95 may include longitudinal slots. The longitudinal slots may extend across (and underneath) the circumferential slots of the shift collar 42. The ends of the wire 18 may extend in a radial outward direction from the shift ring 12, through the longitudinal slots of the driver housing 95 and into the circumferential slots of the shift collar 42.

A user may rotate the mode ring 45 (and thus the shift collar 42) relative to the housing 95. At this time, the wire 18 may remain rotationally fixed to the housing 95 via the longitudinal slots. During this relative rotation, the ends of the wire 18 may slide through the circumferential slots of the shift collar 42. The shapes of the circumferential slots of the shift collar 42 may influence the wire 18 (and thus the shift ring 12) to the desired axial position. In this regard, the ends of the wire 18 may serve as cam followers and the corresponding circumferential slots may serve as cams. It will be appreciated that the circumferential slots of the shift collar 42 may extend in axial directions to thereby axially displace the shift ring 12.

The driver housing 95 may include mounts 48 supporting a lock ring 96. Each mount 48 may include an aperture into which a leg 97 of the lock ring 96 may be slidably inserted. In this way, the lock ring 96 may be rotationally grounded to the driver housing 95, and at the same time the lock ring 96 may be movable in an axial direction and relative to the driver housing 95. A spring 99 may be mounted on the leg 97 of the lock ring 96 and compressed between the lock ring 96 and the mount 48. The lock ring 96 may include lugs 98 that extend in an axial rearward direction. The rearward facing lugs 98 of the lock ring 96 may cooperate with the forward facing lugs 15 of the shift ring 12, as discussed in detail below.

B. The Operation:

The tool chuck 50 may operate differently depending on the axial position of shift ring 12, which may assume three different operating positions inclusive of a DRILL/DRIVE MODE, a MANUAL OVERRIDE MODE and a CHUCK MODE.

FIG. 4 illustrates the shift ring 12 in the DRILL/DRIVE MODE, in which the shift ring 12 may be located at an axial intermediate position. Here, the shift ring 12 may be disengaged from (and rotatable relative to) the lock ring 96 (and thus the driver housing 95). The radial inward facing splines 13 of the shift ring 12 may engage with the radial outward facing splines 24 of the output coupling 20, the radial outward facing splines 34 of the PTO drive disk 30 and the radial outward facing splines 78 of the disk 74. Thus, the shift ring 12, the output coupling 20 (and therefore the input shaft 60), the PTO drive disk 30 and the disk 74 (and therefore the third stage carrier 72) may be rotationally fixed together and rotatable as a unit. Because the PTO drive disk 30 (and therefore the PTO actuator shaft 40 and the chuck actuating shaft 64) and the output coupling 20 (and therefore the input shaft 60 and the chuck actuating screw 55) may be rotationally locked together, the tool chuck 50 may not loosen during operation. A user may then power up the driver to rotationally drive the tool chuck 50.

Figure 5:
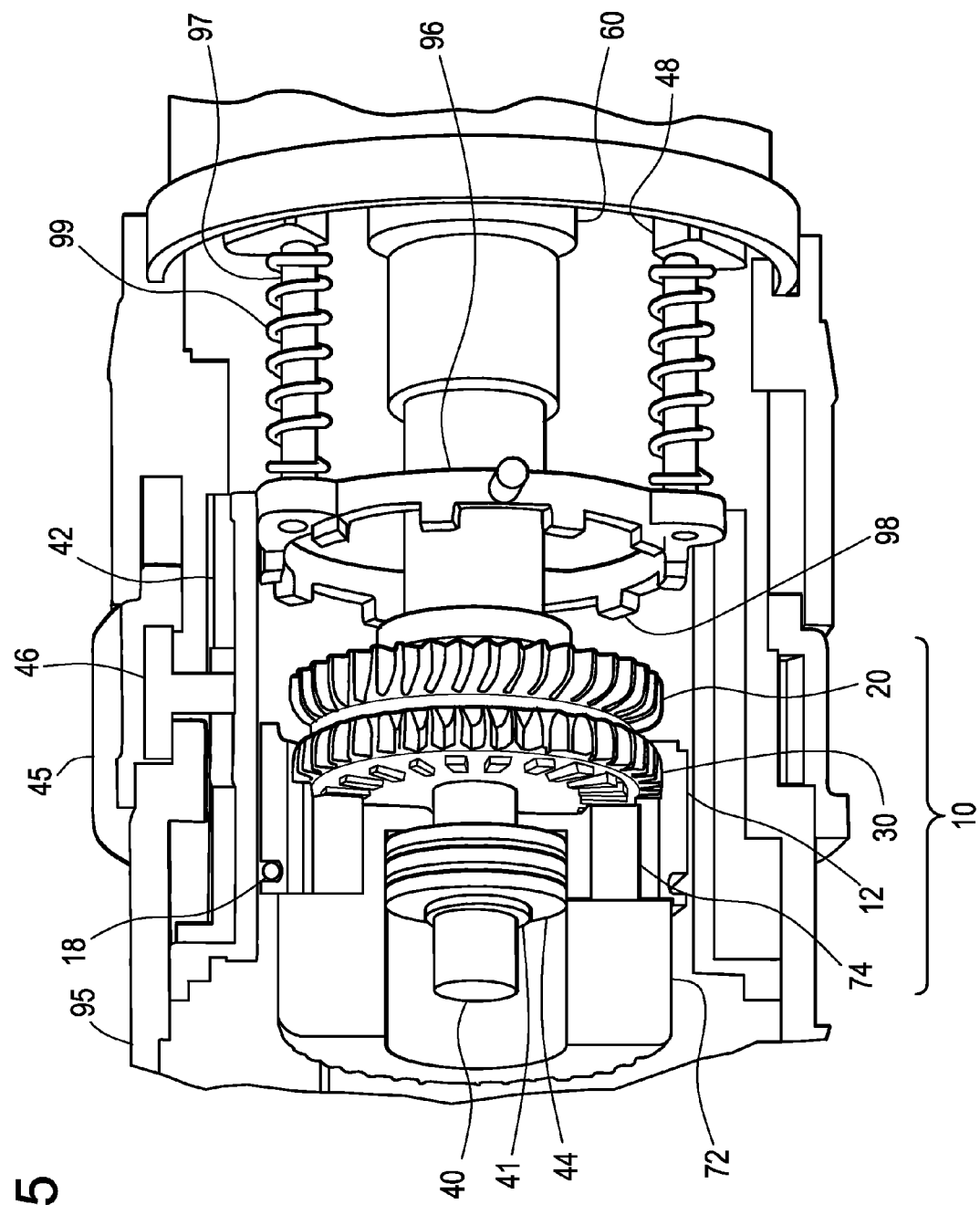
FIG. 5 is a sectional view of the power take off mechanism in a MANUAL OVERRIDE MODE.

FIG. 5 illustrates the shift ring 12 in the MANUAL OVERRIDE MODE, in which the shift ring 12 may be located at an axial rearward position. Here, the radial inward facing splines 13 of the shift ring 12 may engage with the radial outward facing splines 34 of the PTO drive disk 30 and the radial outward facing splines 78 of the disk 74. Thus, the shift ring 12, the PTO drive disk 30 (and therefore the PTO actuator shaft 40) and the disk 74 (and therefore the third stage carrier 72) may be rotationally locked together.

A user may grasp and manually rotate the input shaft 60 (together with the chuck jaws and the chuck actuating screw 55) relative to the driver housing 95. At this time, transmission and motor drag may prevent the PTO actuator shaft 40 (and thus the chuck actuating shaft 64) from rotating relative to the driver housing 95 so that the chuck actuating screw 55 may rotate relative to the chuck actuating shaft 64. This relative rotation may cause the chuck actuating screw 55 to advance or retract in the axial direction (depending on the rotation direction of the input shaft 60) by virtue of the interaction between the radially inward facing threads 68 and the radially outward facing threads 58. The translational movement of the chuck actuating screw 55 may push or pull on the chuck jaws to open or close the same.

For example, during a closing operation, the chuck actuating screw 55 (together with the chuck jaws) may be advanced in the axial direction. During this time, the passageways of the nose portion of the input shaft 60 may influence the chuck jaws in a radial inward direction through the radial passageways 56 of the chuck actuating screw 55. This pusher type jaw action is well known in the pertinent art.

Figure 6:
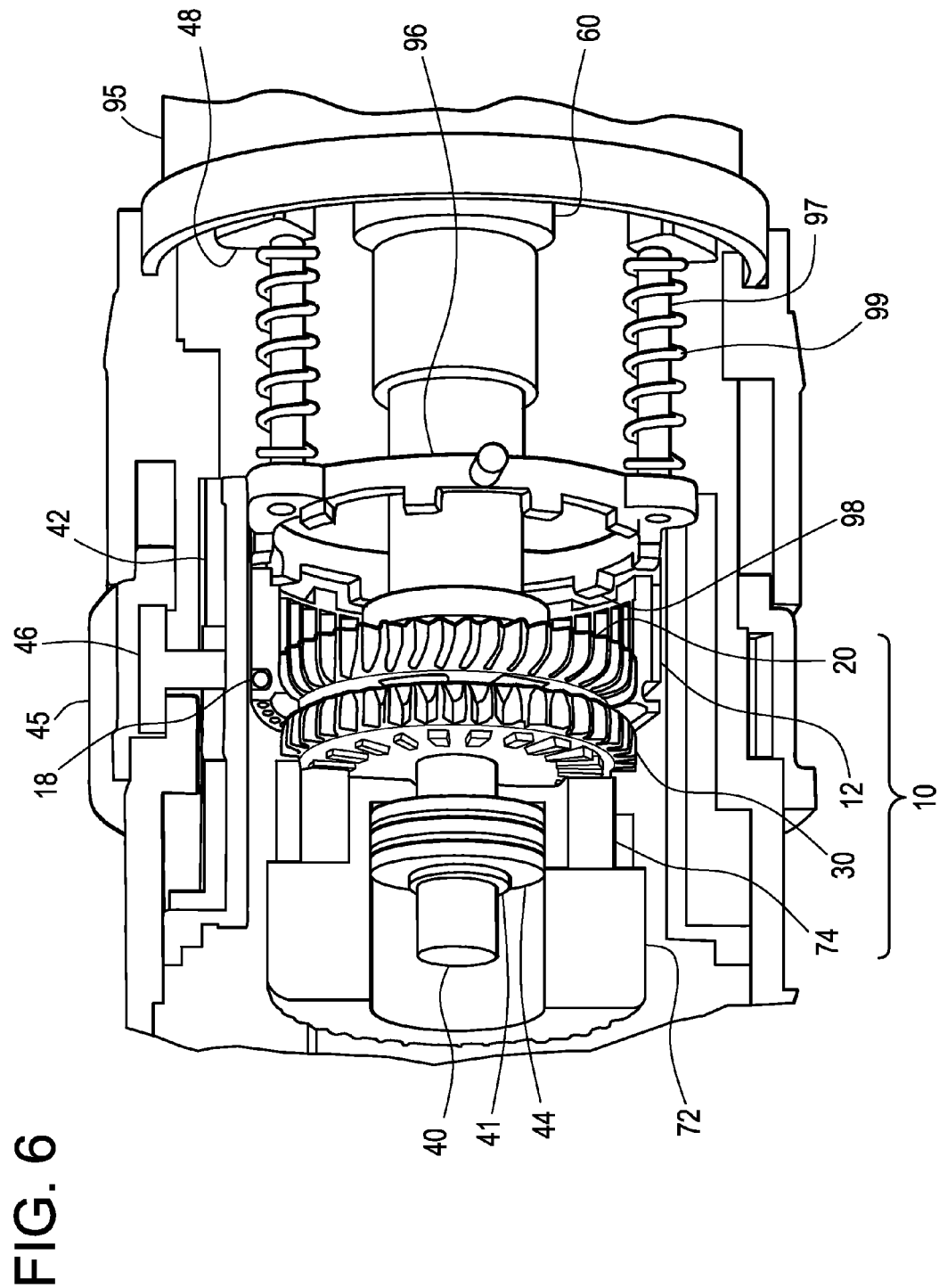
FIGS. 6 and 7 are sectional view of the power take off mechanism in a CHUCK MODE.

FIG. 6 illustrates the shift ring 12 in the CHUCK MODE, in which the shift ring 12 may be located at an axial forward position. Here, the forward facing lugs 15 of the shift ring 12 may engage with the rearward facing lugs 98 of the lock ring 96 to rotationally ground the shift ring 12 to the driver housing 95. If the shift ring 12 is properly clocked to (or angularly positioned relative to) the lock ring 96, then the lugs 15 may enter into the spaces between the lugs 98 to achieve the desired engagement. However, as shown in FIG. 6, the angular position of the shift ring 12 (relative to the lock ring 96) may be such that the lugs 15, 98 hit in a head-to-head fashion. In this condition, the shift ring 12 may drive the lock ring 96 in an axial forward direction and against the influence of the springs 99. The mounts 48 of the driver housing 95 may guide the axial travel of the lock ring 96. In this way, the shift ring 12 may be located in the desired forward axial position, notwithstanding the head-to-head collision of the lugs 15, 98. Thus, the lock ring 96 may offer a "compliant grounding" feature to the extent that the lock ring 96 may give way to the forward axial travel of the shift ring 12.

In the condition shown in FIG. 6, the radial inward facing splines 13 of the shift ring 12 may engage with the radial outward facing splines 24 of the output coupling 20. However, as noted above, the shift ring 12 is not yet rotationally grounded to the lock ring 96 (and thus the driver housing 95). Thus, the shift ring 12, the output coupling 20, the PTO drive disk 30 and the disk 74 may be rotatable relative to the driver housing 95.

A user may then power up the driver to actuate the tool chuck 50. The third stage carrier 72 may rotationally drive the PTO drive disk 30 via the cooperating clutch features 79, 36 respectively provided on the confronting surfaces of the disk 74 and the PTO drive disk 30. The PTO drive disk 30 may rotationally drive the PTO actuator shaft 40, which in turn may rotationally drive the chuck actuating shaft 64. Due to frictional drag (e.g., between the cooperating threads of the chuck actuating shaft 64 and the chuck actuating screw 55), the chuck actuating shaft 64 may rotate together with the input shaft 60 (and thus the output coupling 20 and the shift ring 12). The shift ring 12 may rotate relative to the lock ring 96 until the shift ring 12 is properly clocked to (or angularly positioned relative to) the lock ring 96, as shown in FIG. 7.

Figure 7:
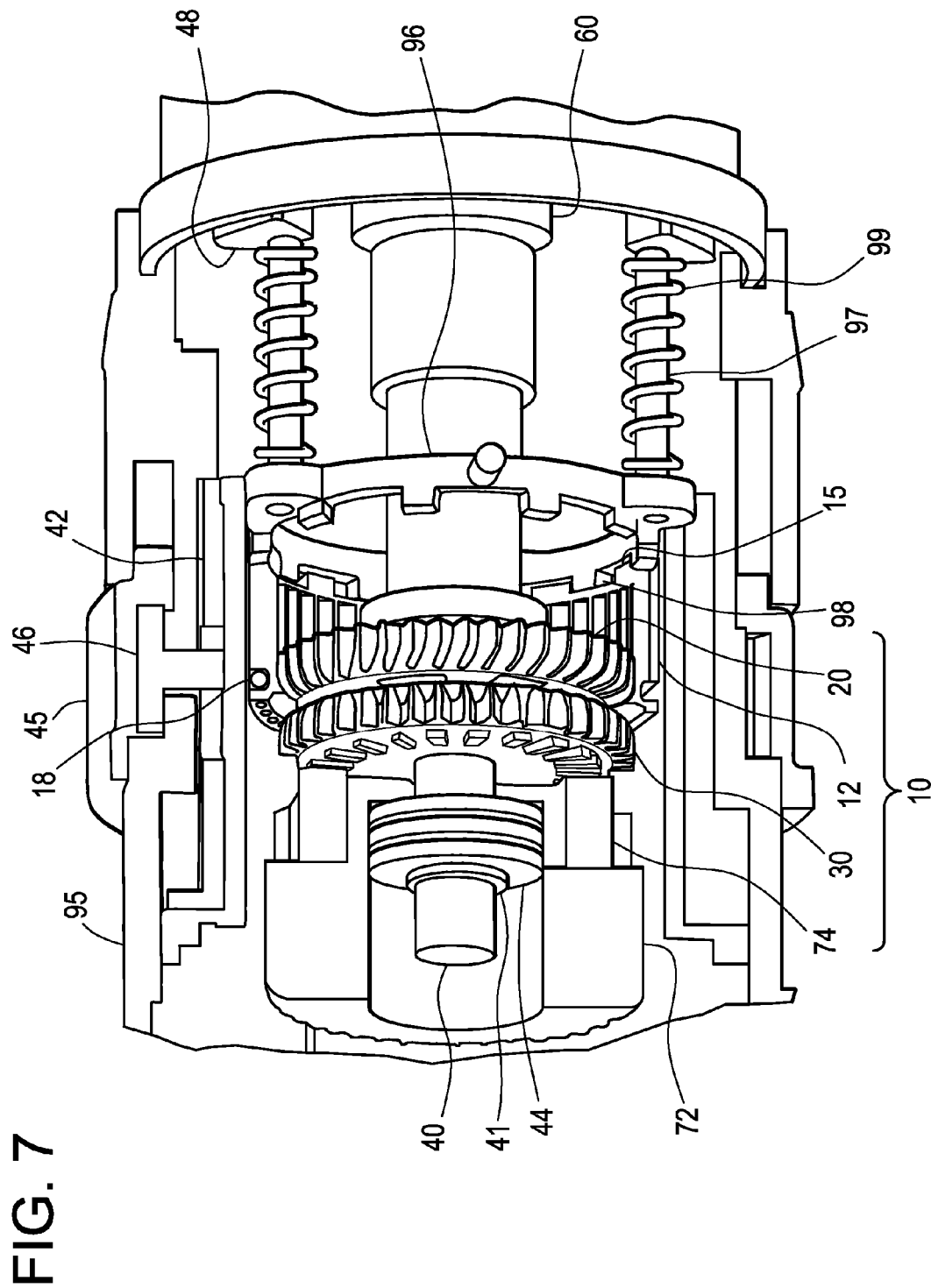

With reference to FIG. 7, the lugs 15 of the shift ring 12 may become aligned with the spaces between the lugs 98 of the lock ring 96. At this time, the springs 99 may influence the lock ring 96 in an axial rearward direction causing the lugs 15 to enter into the spaces between the lugs 98. In this condition, the shift ring 12 and the output coupling 20 (and therefore the input shaft 60 and the chuck actuating screw 55) may be rotationally grounded to the driver housing 95.

The third stage carrier 72 may continue to rotationally drive the PTO drive disk 30, which in turn may continue to rotationally drive the PTO actuator shaft 40, which in turn may continue to rotationally drive the chuck actuating shaft 64. Here, the chuck actuating shaft 64 may rotate relative to the chuck actuating screw 55, which may remain rotationally grounded to the driver housing 95 (via the chuck jaws, the input shaft 60, the output coupling 20, the shift ring 12 and the lock ring 96). This relative rotation may cause the chuck actuating screw 55 to advance or retract in the axial direction (depending on the rotation direction of the chuck actuating shaft 64) by virtue of the interaction between the radial inward facing threads 68 and the radial outward facing threads 58. The translational movement of the chuck actuating screw 55 may push or pull on the chuck jaws to open or close the same.

During chuck actuation, the input shaft 60, the chuck jaws and the chuck actuating screw 55 may remain rotationally grounded to the driver housing 95, while the chuck actuating screw 55 may move axially (via the rotational movements of the chuck actuating shaft 64) relative to the input shaft 60 to open and close the chuck jaws. This may be referred to as a dead spindle feature since the user may not be exposed to (or observe) any rotating parts.

Once the tool chuck 50 is tight (i.e., when the chuck jaws clamp the accessory) or fully opened, the cooperating clutch features 79, 36 respectively provided on the confronting surfaces of the disk 74 and the PTO drive disk 30 may give way and slip relative to each other. At this time, the PTO drive disk 30 (together with the PTO actuator shaft 40) may move in an axial forward direction against the influence of the spring 44. When the cooperating clutch features 79, 36 slip, they may produce an audible indication that the chuck actuation process is complete.

The cooperating clutch features 79 and 36 may give way or slip at a predetermined torque threshold. The predetermined torque threshold may be suitably adjusted by selecting an appropriate spring 44 and/or by suitably designing the geometries of the cooperating clutch features 79, 36. Further, the predetermined torque threshold for tightening the tool chuck 50 may be less than the predetermined torque threshold for loosening the tool chuck 50. This feature may be obtained by suitably designing the geometries of the cooperating clutch features 79, 36. Numerous and varied clutch surface geometries are well known in this art, and therefore a detailed discussion of the same is omitted.

II. Example Embodiment Depicted in FIGS. 8-9

Figure 8:
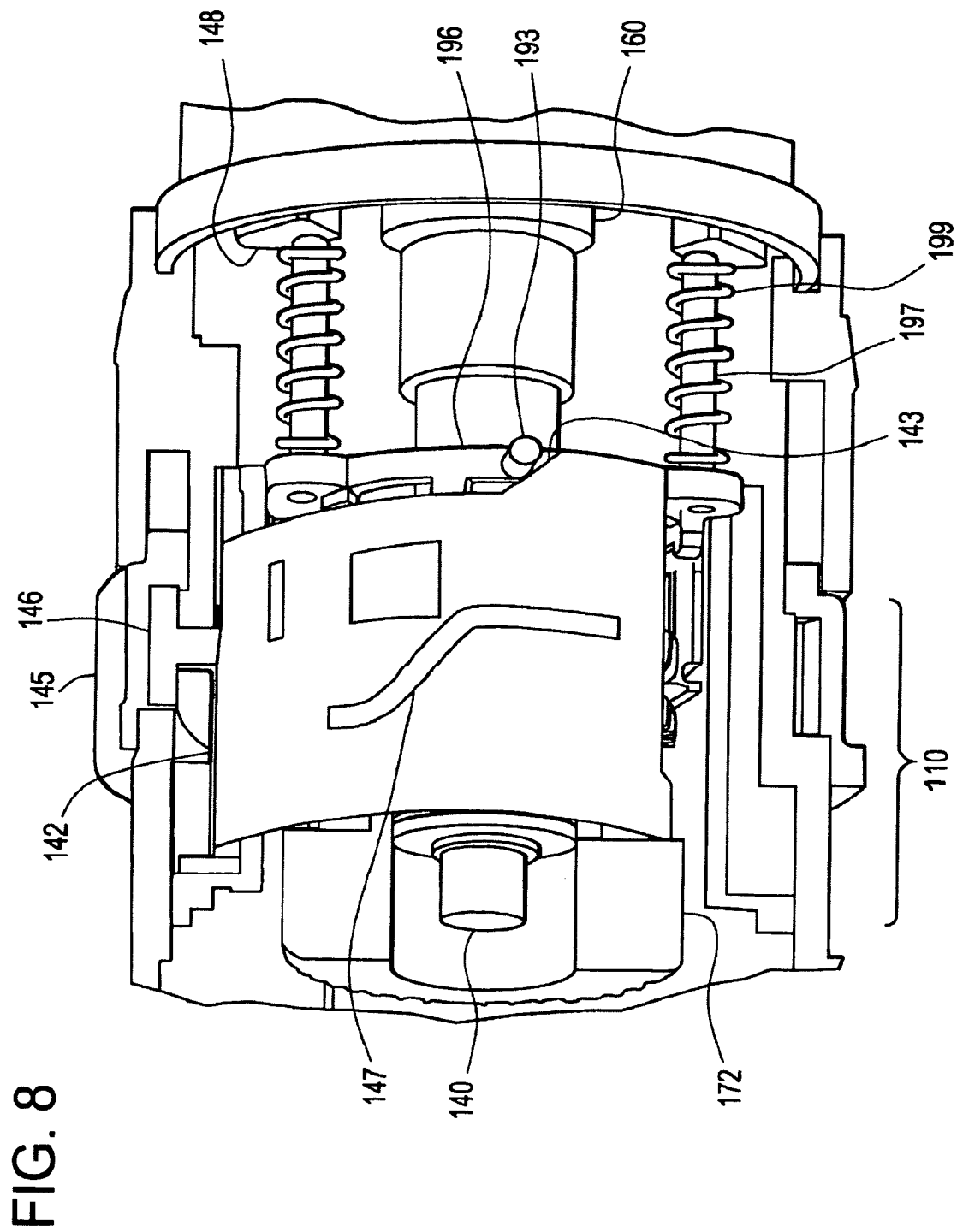
FIGS. 8-9 are schematic views of a tool chuck with a power take off mechanism according to another example, non-limiting embodiment.
Figure 9:
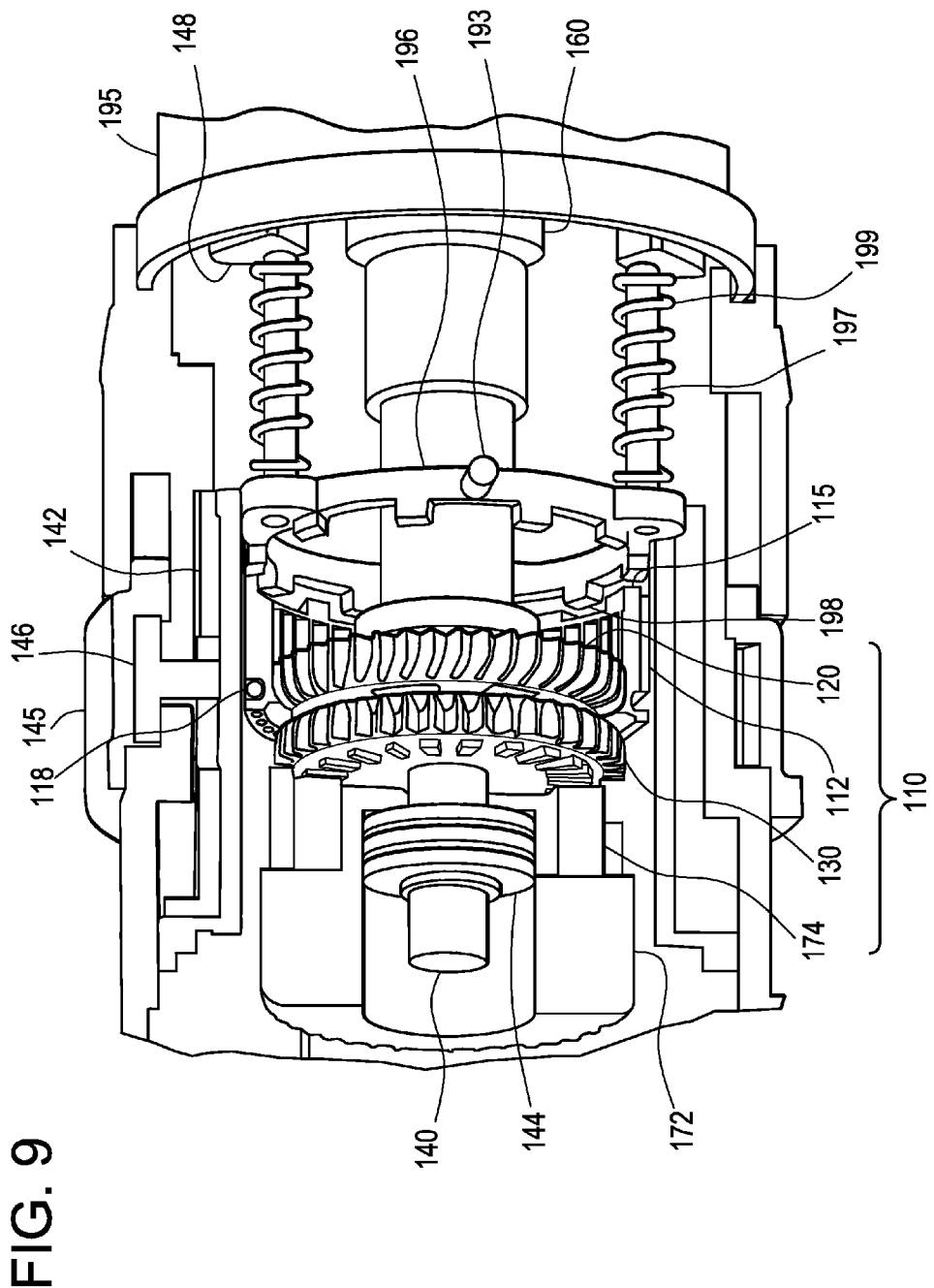

FIGS. 8-9 show another example, non-limiting embodiment of a PTO mechanism 110 that may support a tool chuck. This example embodiment is similar to the one noted in section I above to the extent that the tool chuck may be operated in three different modes inclusive of the DRILL/DRIVE MODE, the MANUAL OVERRIDE MODE and the CHUCK MODE. In this example embodiment, however, the shift ring may assume two different axial positions.

A. The Structure:

With reference to FIG. 8, the shift collar 142 may include a slot 147 that extends in a circumferential direction around the shift collar 142. The slot 147 may receive the ends of the wire 118 (see FIG. 9) mounted on the shift ring 112. Upon rotating the shift collar 142, the slot 147 may influence the wire 118 (and thus the shift ring 112) to the desired axial positions, as will be discussed in more detail below.

The shift collar 142 may also include a cam surface 143 that interacts with a pin 193 extended from the lock ring 196. In all other respects, this example embodiment may be structurally similar to the previous example embodiment.

B. The Operation:

In the DRILL/DRIVE MODE, the shift ring 112 may be located at an axial intermediate position. Here, the shift ring 112 may be disengaged from (and rotatable relative to) the lock ring 196 (and thus the driver housing 195). The radial inward facing splines of the shift ring 112 may engage with the radial outward facing splines of the output coupling 120, the radial outward facing splines of the PTO drive disk 130 and the radial outward facing splines of the disk 174. Because the PTO drive disk 130 (and therefore the PTO actuator shaft 140 and the chuck actuating shaft) and the output coupling 120 (and therefore the input shaft 160 and the chuck actuating screw) may be rotationally locked together, the tool chuck may not loosen during operation. A user may then power up the driver to rotationally drive the tool chuck.

FIG. 9 illustrates the PTO mechanism 110 in the MANUAL OVERRIDE MODE. Here, the mode ring 145 (and thus the shift collar 142) may be rotated to influence the shift ring 112 to an axial forward position. The radial inward facing splines of the shift ring 112 may engage with the radial outward facing splines of the output coupling 120. At the same time, the cam surface 143 of the shift collar 142 (see FIG. 8) may slide across the pin 193 to influence the lock ring 196 in an axial forward direction. In this condition, the shift ring 112 may be disengaged from (and rotatable relative to) the lock ring 196 (and thus the driver housing 195).

A user may grasp and manually rotate the input shaft 160 (together with the chuck jaws and the chuck actuating screw) relative to the driver housing 195. At this time, transmission and motor drag may prevent the PTO actuator shaft 140 (and thus the chuck actuating shaft) from rotating relative to the driver housing 195 so that the chuck actuating screw may rotate relative to the chuck actuating shaft. This relative rotation may cause the chuck actuating screw to advance or retract in the axial direction (depending on the rotation direction of the input shaft 160). The translational movement of the chuck actuating screw may push or pull on the chuck jaws to open or close the same.

In the MANUAL OVERRIDE MODE depicted in FIG. 9, the shift ring 112 (in the axial forward position) may be disengaged from the PTO drive disk 130 and the disk 174. Accordingly, the cooperating clutch features of the PTO drive disk 130 and the disk 174 may give way or slip to prevent the system from being over torqued manually and/or in the event that the driver is inadvertently powered up.

The CHUCK MODE may be achieved rotating the mode ring 145 (and thus the shift collar 142) so that the cam surface 143 of the shift collar 142 (see FIG. 8) may slide back across the pin 193 allowing the spring 199 to influence the lock ring 196 in an axial rearward direction. Here, the shift ring 112 may remain at the axial forward position.

The forward facing lugs 115 of the shift ring 112 may engage with the rearward facing lugs 198 of the lock ring 196 to rotationally ground the shift ring 112 to the driver housing 195. If the shift ring 112 is properly clocked to (or angularly positioned relative to) the lock ring 196, then the lugs 115 may enter into the spaces between the lugs 198 to achieve the desired engagement. However, the angular position of the shift ring 112 (relative to the lock ring 196) may be such that the lugs 115, 198 hit in a head-to-head fashion.

A user may then power up the driver to actuate the tool chuck. The third stage carrier 172 may rotationally drive the PTO drive disk 130. The PTO drive disk 130 may rotationally drive the PTO actuator shaft 140, which in turn may rotationally drive the chuck actuating shaft. Due to frictional drag (e.g., between the cooperating threads of the chuck actuating shaft and the chuck actuating screw), the chuck actuating shaft may rotate together with the input shaft 160 (and thus the output coupling 120 and the shift ring 112). The shift ring 112 may rotate relative to the lock ring 196 until the shift ring 112 is properly clocked to (or angularly positioned relative to) the lock ring 196. At this time, the springs 199 may influence the lock ring 196 in an axial rearward direction causing the lugs 115 to enter into the spaces between the lugs 198. In this condition, the shift ring 112 and the output coupling 120 (and therefore the input shaft 160 and the chuck actuating screw) may be rotationally grounded to the driver housing 195.

The third stage carrier 172 may continue to rotationally drive the PTO drive disk 130, which in turn may continue to rotationally drive the PTO actuator shaft 140, which in turn may continue to rotationally drive the chuck actuating shaft. Here, the chuck actuating shaft may rotate relative to the chuck actuating screw, which may remain rotationally grounded to the driver housing 195 (via the chuck jaws, the input shaft 160, the output coupling 120, the shift ring 112 and the lock ring 196). This relative rotation may cause the chuck actuating screw to advance or retract in the axial direction (depending on the rotation direction of the chuck actuating shaft). The translational movement of the chuck actuating screw may push or pull on the chuck jaws to open or close the same.

Once the tool chuck is tight (i.e., when the chuck jaws clamp the accessory) or fully opened, the cooperating clutch features of the disk 174 and the PTO drive disk 130 may give way and slip relative to each other, which may produce an audible indication that the chuck actuation process is complete.

Figure 10:
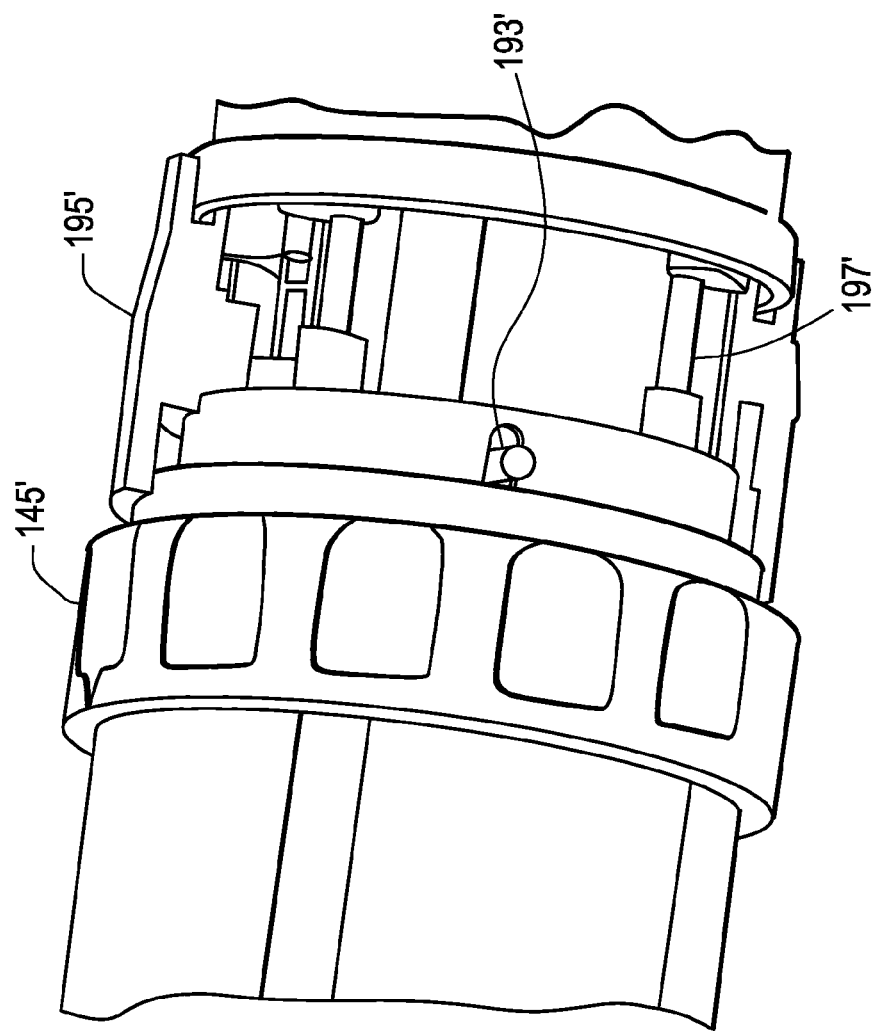
FIGS. 10-11 are schematic view of an example modification of a lock ring depicted in FIGS. 8-9.
Figure 11:
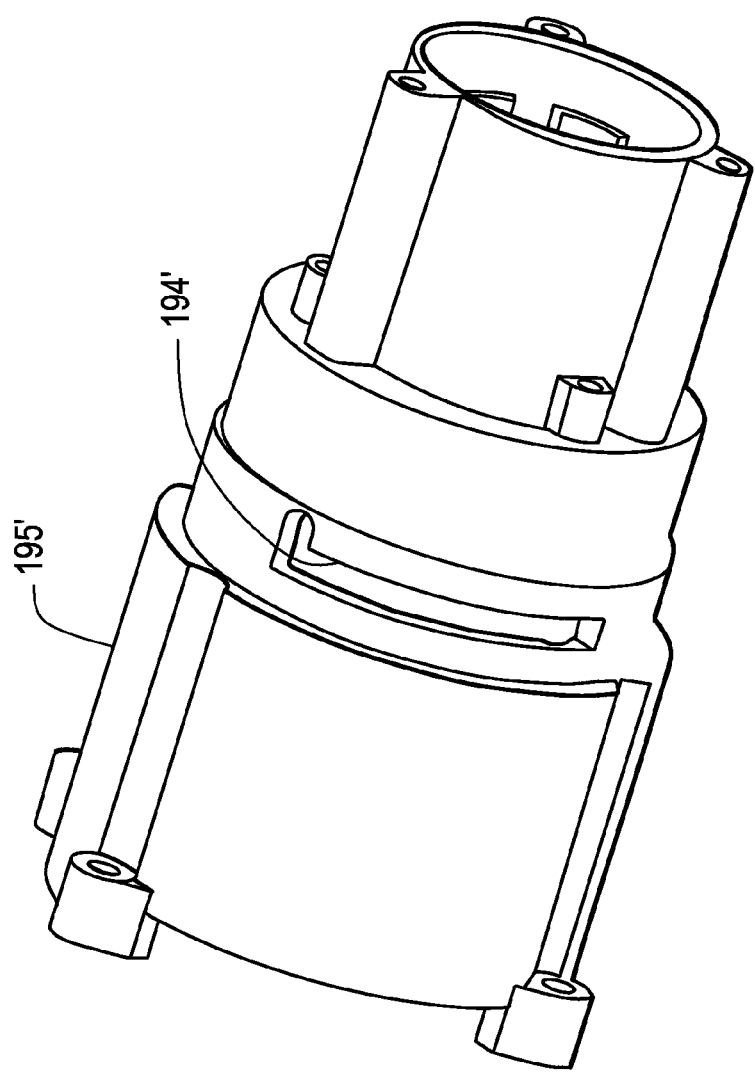

III. Example Modification for Lock Ring—FIGS. 10-11:

FIGS. 10-11 illustrate an example modification of the lock ring depicted in FIGS. 8-9. Here, and with reference to FIG. 10, the pin 193' of the lock ring may extend in a radial outward direction and through a slot in the housing 195'. In this example embodiment, the pin 193' may interact with the axial forward facing surface of the mode ring 145' (instead of a cam surface on the shift collar, as in FIGS. 8-9).

As shown in FIG. 11, the slot 194' in the housing 195' may include an axial portion to accommodate an axial travel of the pin 193', and a circumferential portion to accommodate a circumferential travel of the radial extension (which rotationally fixes together the mode ring 145' and the shift collar).

The user may rotate the mode ring 145' (and thus the shift collar) relative to the housing 195' to influence the shift ring to the intermediate and forward axial positions to respectively achieve the DRILL DRIVE MODE and the CHUCK MODE. During this relative rotation, the axial forward facing surface of the mode ring 145' may slide across the pin 193' of the lock ring, and the radial extension (interconnecting the mode ring 145' and the shift collar) may travel through the circumferential portion of the slot 194'.

In the CHUCK MODE, the shift ring may be located in the axial forward position so that the forward facing lugs of the shift ring may engage with the rearward facing lugs of the lock ring to rotationally ground the shift ring to the driver housing. The user may then slide the mode ring 145' (relative to the housing 195') to an axial forward position to achieve the MANUAL OVERRIDE MODE.

The mode ring 145' (which may travel axially relative to the shift collar) may push the pin 193' (and the lock ring) to an axial forward position. During the forward axial movement of the lock ring, the pin 193' may travel through the axial portion of the slot 194' in the housing 195', and the shift ring 112' may be disengaged from (and rotatable relative to) the lock ring 196' (and thus the driver housing 195').

While holding the mode ring 145' in the forward axial position, the user may grasp and manually rotate the input shaft (together with the chuck jaws and the chuck actuating screw) relative to the driver housing 195'. At this time, transmission and motor drag may prevent the PTO actuator shaft (and thus the chuck actuating shaft) from rotating relative to the driver housing 195' so that the chuck actuating screw may rotate relative to the chuck actuating shaft. This relative rotation may cause the chuck actuating screw to advance or retract in the axial direction (depending on the rotation direction of the input shaft). The translational movement of the chuck actuating screw may push or pull on the chuck jaws to open or close the same.

When the user releases the mode ring 145', the springs on the legs 197' of the lock ring may drive the lock ring (and thus the mode ring 145') in the axial rearward direction.

IV. Example Embodiment depicted in FIGS. 12-18

FIGS. 12-18 show another example, non-limiting embodiment of a PTO mechanism 210 that may support a tool chuck. This example embodiment is similar to the one noted in section I above to the extent that the tool chuck may be operated in three different modes inclusive of the DRILL/DRIVE MOE, the MANUAL OVERRIDE MODE and the CHUCK MODE. But there are some notable differences.

Figure 12:
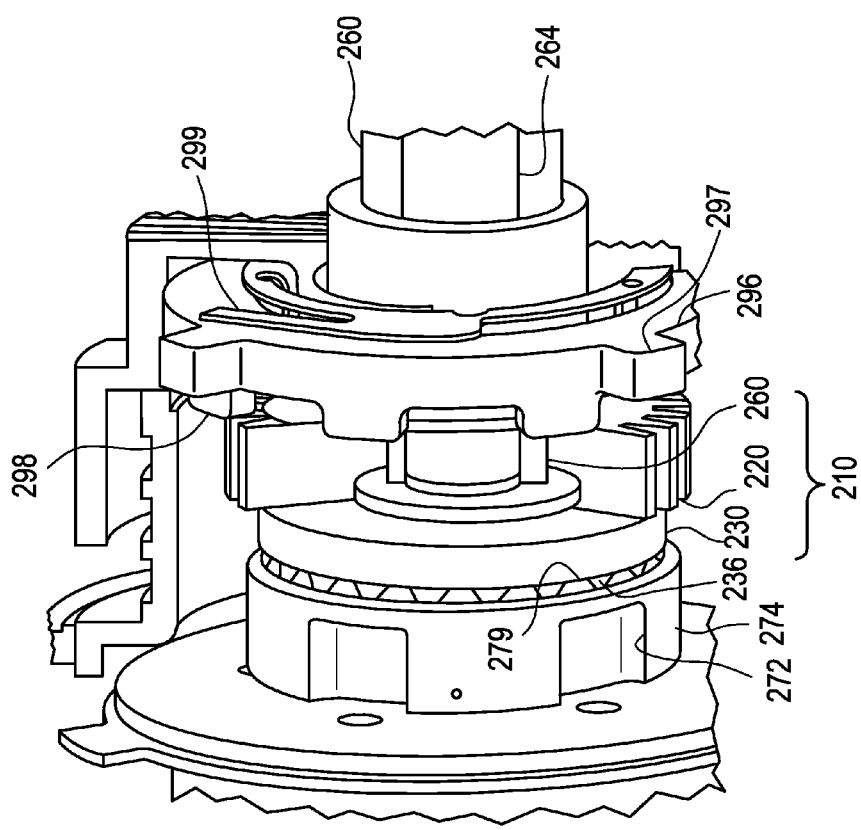
FIGS. 12-18 are schematic views of a tool chuck with a power take off mechanism according to another example, non-limiting embodiment.

A. The Structure:

As shown in FIG. 12, the PTO mechanism 210 may include an output coupling 220 and a PTO drive disk 230. And with reference to FIG. 13, the PTO mechanism 210 may also include a shift ring 212.

The shift ring 212 may have a radial inward facing surface provided with splines that engage with radial outward facing splines of the output coupling 220. In this way, the shift ring 212 may be rotationally fixed to (and axially moveable relative to) the output coupling 220. The shift ring 212 may also include axial forward facing lugs 215 that may selectively engage with a lock ring 296, and axial rearward facing lugs 216 that may selectively engage with a drive ring 275 mounted on a disk 274 of the third stage carrier (not shown). The shift ring 212 may have a continuous circumferential groove 217 for accommodating a wire (not shown).

The wire, which may be slidable through the circumferential groove 217, may have free ends that extend in a radial direction and out of the circumferential groove 217. The fee ends of the wire (serving as cam followers) may be received in a slot of a shift collar (not shown) rotatably mounted on the driver housing. Upon rotating the shift collar, the slot may influence the cam followers (and thus the shift ring 212) to the desired axial positions, as will be discussed in more detail below.

As shown in FIG. 12, the output coupling 220 may be fixedly mounted on an input shaft 260 of the tool chuck. And the PTO drive disk 230 may be rotationally coupled to a chuck actuating shaft 264 of the tool chuck via a PTO actuator shaft (similar to the PTO actuator shaft 40 depicted in FIG. 3). The PTO drive disk 230 may have an axial rearward facing surface provided with clutch features 236 that cooperate with corresponding clutch features 279 provided on a axial forward facing surface of the disk 274.

Figure 13:
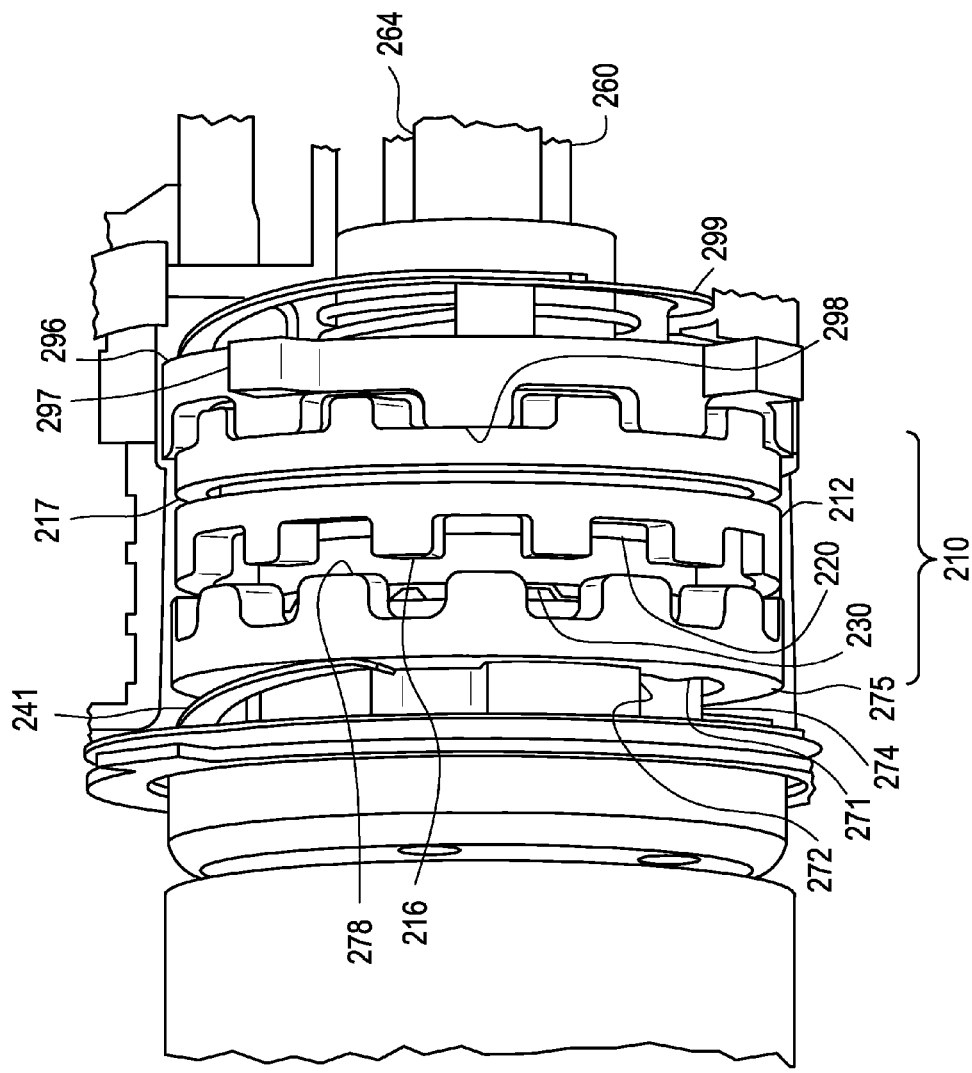

As shown in FIG. 13, the drive ring 275 may include radial inward facing lugs 271 that engage with radial outward facing grooves 272 in the disk 274. In this way, the drive ring 275 may be rotationally fixed to (and axially moveable relative to) the disk 274. A spring 241 may be captured between the third stage carrier and the drive ring 275 to influence the drive ring 275 in an axial forward direction. The drive ring 275 may include axial forward facing lugs 278 that selectively cooperate with the axial rearward facing lugs 216 of the shift ring 212.

The lock ring 296 may include radial outward facing tabs 297 that engage with radial inward facing grooves (not shown) of the driver housing. In this way, the lock ring 296 may be rotationally fixed to (and axially moveable relative to) the driver housing. A spring 299 may be captured between the driver housing and the lock ring 296 to influence the lock ring 296 in an axial rearward direction. The lock ring 296 may include axial rearward facing lugs 298 that selectively cooperate with the axial forward facing lugs 215 of the shift ring 212.

In this example embodiment, the tool chuck may be somewhat similar to the one described above in section I. Briefly, the tool chuck may include the input shaft 260. A forward end of the input shaft 260 may support a nose portion (not shown) that may include passageways through which chuck jaws (not shown) are respectively slidable. The passageways of the nose portion may rotationally fix the input shaft 260 to the chuck jaws. The input shaft 260 may include a through bore that rotatably supports the chuck actuating shaft 264. And the chuck actuating shaft 264 may support a PTO actuator shaft.

The chuck actuating shaft 264 may include a through bore with radial inward facing threads that may interact with radial outward facing threads of a chuck actuating screw (not shown). The chuck actuating screw may include radial passageways through which the chuck jaws are respectively slidable. The radial passageways may rotationally fix the chuck actuating screw to the chuck jaws.

As shown in FIGS. 12 and 13, the output coupling 220, the PTO drive disk 230, the disk 274 of the third stage carrier and the drive ring 275 may be assembled together in a coaxial fashion. Here, the clutch features 236 of the PTO drive disk 230 may face (and engage with) the clutch features 279 of the disk 274.

The shift ring 212 may be mounted on the output coupling 220 for axial movement to (1) a forward axial position in which the axial forward facing lugs 215 of the shift ring 212 may engage with the axial rearward facing lugs 298 of the lock ring 296, (2) an intermediate axial position in which the shift ring 212 may be disengaged from the lock ring 296 and the drive ring 275 and (3) an rearward axial position in which the axial rearward facing lugs 216 may engage with the axial forward facing lugs 278 of the drive ring 275. In all three axial positions, the radial inward facing splines of the shift ring 212 may remain engaged with the radial outward facing splines of the output coupling 220 so that the shift ring 212 and the output coupling 220 may remain rotationally locked together.

As in the previous embodiments, the driver housing may support a mode ring (not shown) and a shift collar (not shown), which may be manipulated by a user to axially position the shift ring 212 to achieve the various operational modes.

B. The Operation:

The tool chuck may operate differently depending on the axial position of shift ring 212, which may assume three different operating positions inclusive of a DRILL/DRIVE MODE, a MANUAL OVERRIDE MODE and a CHUCK MODE.

Figure 14:
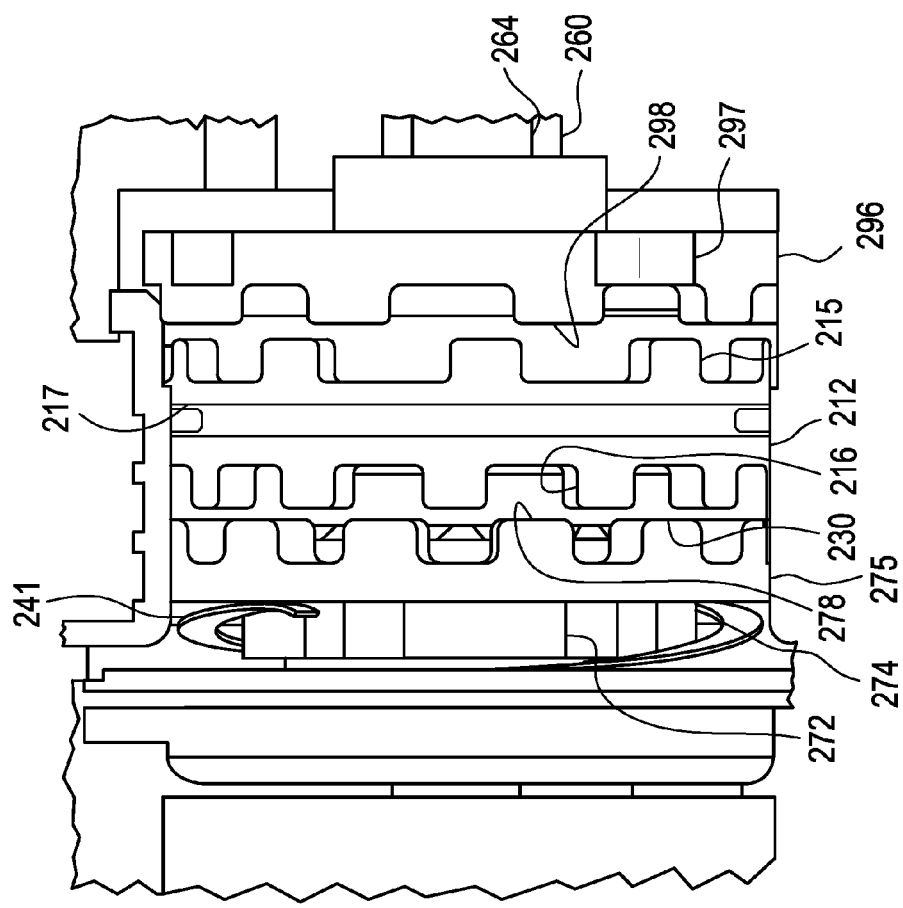

FIG. 14 illustrates the shift ring 212 in the MANUAL OVERRIDE MODE, in which the shift ring 212 may be located at the intermediate axial position. Here, the shift ring 212 may be disengaged from the lock ring 296 and the drive ring 275. In this condition, the shift ring 112 (and thus the output coupling 220 and the input shaft 260) may be rotatable relative to the driver housing.

A user may grasp and manually rotate the input shaft 260 (together with the chuck jaws and the chuck actuating screw) relative to the driver housing. At this time, transmission and motor drag may prevent the disk 274 (and thus the PTO drive disk 230 and the chuck actuating shaft 264) from rotating relative to the driver housing so that the chuck actuating screw may rotate relative to the chuck actuating shaft 264. This relative rotation may cause the chuck actuating screw to advance or retract in the axial direction (depending on the rotation direction of the input shaft 260). The translational movement of the chuck actuating screw may push or pull on the chuck jaws to open or close the same.

In the MANUAL OVERRIDE MODE depicted in FIG. 14, the shift ring 212 may be disengaged from the drive ring 275 and the PTO drive disk 230. Accordingly, the cooperating clutch features 236, 279 of the PTO drive disk 230 and the disk 274 may give way or slip to prevent the system from being over torqued manually and/or in the event that the driver is inadvertently powered up.

The DRILL/DRIVE MODE may be achieved by sliding the shift ring 212 to the rearward axial position in which the rearward facing lugs 216 of the shift ring 212 may engage with the forward facing lugs 278 of the drive ring 275. If the shift ring 212 is properly clocked to (or angularly positioned relative to) the drive ring 275, then the lugs 216 may enter into the spaces between the lugs 278 to achieve the desired engagement.

Figure 15:
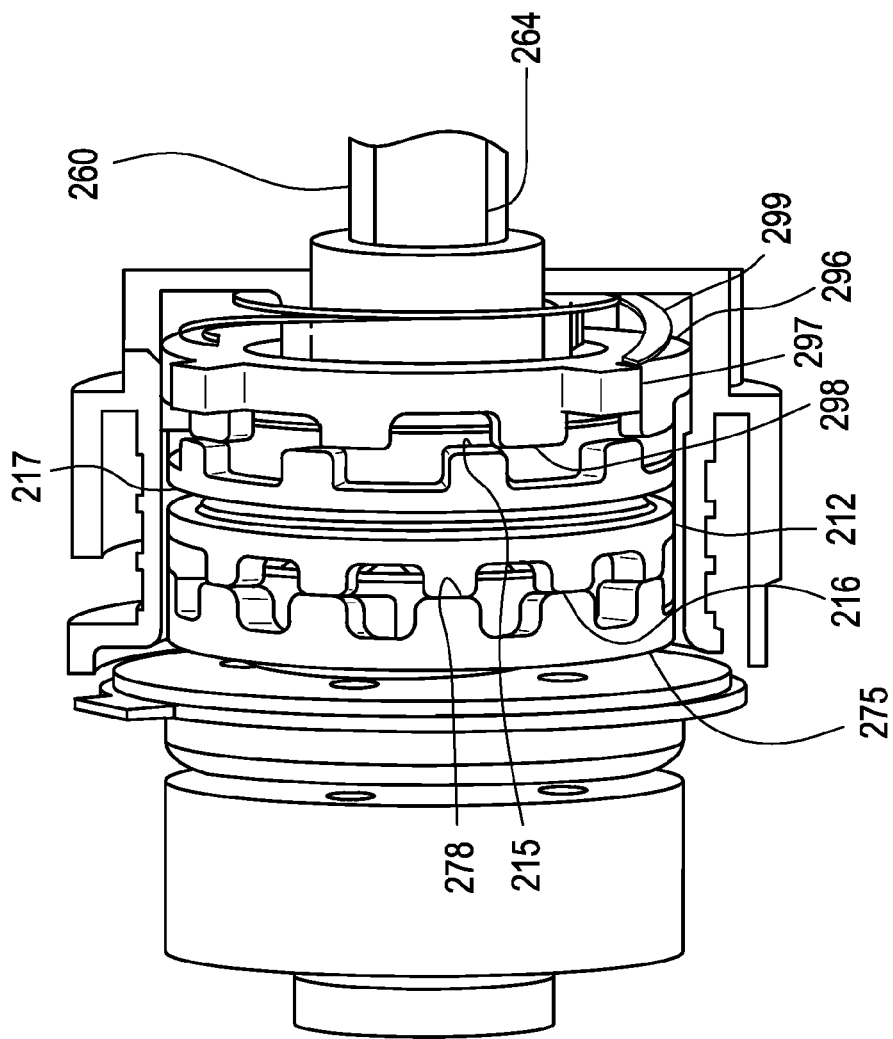

However, as shown in FIG. 15, the angular position of the shift ring 212 (relative to the drive ring 275) may be such that the lugs 216, 278 hit in a head-to-head fashion. In this condition, the shift ring 212 may drive the drive ring 275 in an axial rearward direction and against the influence of the spring 241. The grooves 272 in the disk 274 (see FIG. 12) may guide the axial travel of the drive ring 275. In this way, the shift ring 212 may be located in the desired rearward axial position, notwithstanding the head-to-head collision of the lugs 216, 278. Thus, the drive ring 275 may offer a "compliant engaging" feature to the extent that the drive ring 275 may give way to the rearward axial travel of the shift ring 212.

Figure 16:
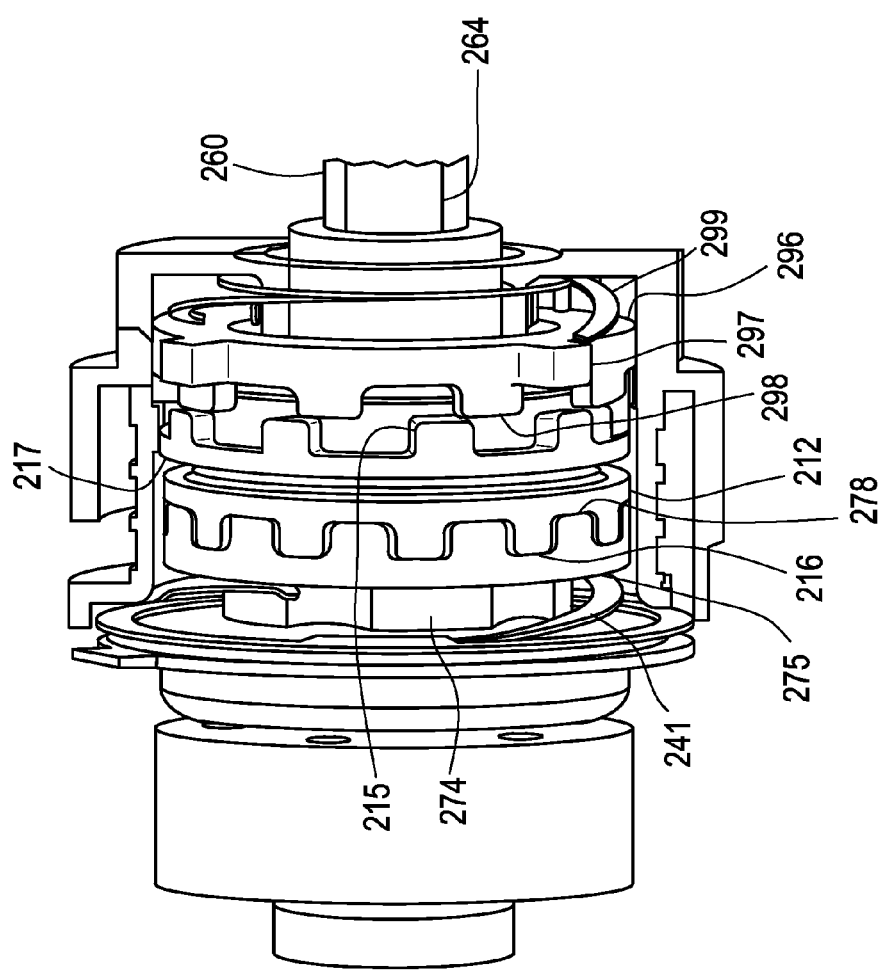

A user may then power up the driver to rotationally drive the disk 274. Initially, the disk 274 may rotationally drive the drive ring 275 (relative to the shift ring 212) until the drive ring 275 is properly clocked to (or angularly positioned relative to) the shift ring 212, as shown in FIG. 16. Here, the lugs 278 of the drive ring 275 may become aligned with the spaces between the lugs 216 of the shift ring 212. At this time, the spring 241 may influence the drive ring 275 in an axial forward direction causing the lugs 278 to enter into the spaces between the lugs 216. In this condition, the drive ring 275 (and thus the disk 274) and the shift ring 212 (and thus the output coupling 220, the input shaft 260 and the chuck actuating screw) may be rotationally locked together. By virtue of the interacting clutch features 279, 236, the disk 274 and the PTO drive disc 230 (and thus the chuck actuating shaft 264) may be rotationally coupled together. Because the disk 274 rotationally drives the input shaft 260 (via the drive ring 275, the shift ring 212 and the output coupling 220) and the chuck actuating shaft 264 (via the PTO drive disk 230 and the PTO actuator shaft), the tool chuck may not loosen during operation.

The CHUCK MODE may be achieved by sliding the shift ring 212 to a forward axial position in which the forward facing lugs 215 of the shift ring 212 may engage with the rearward facing lugs 298 of the lock ring 296 to rotationally ground the shift ring 212 to the driver housing. If the shift ring 212 is properly clocked to (or angularly positioned relative to) the lock ring 296, then the lugs 215 may enter into the spaces between the lugs 298 to achieve the desired engagement.

Figure 17:
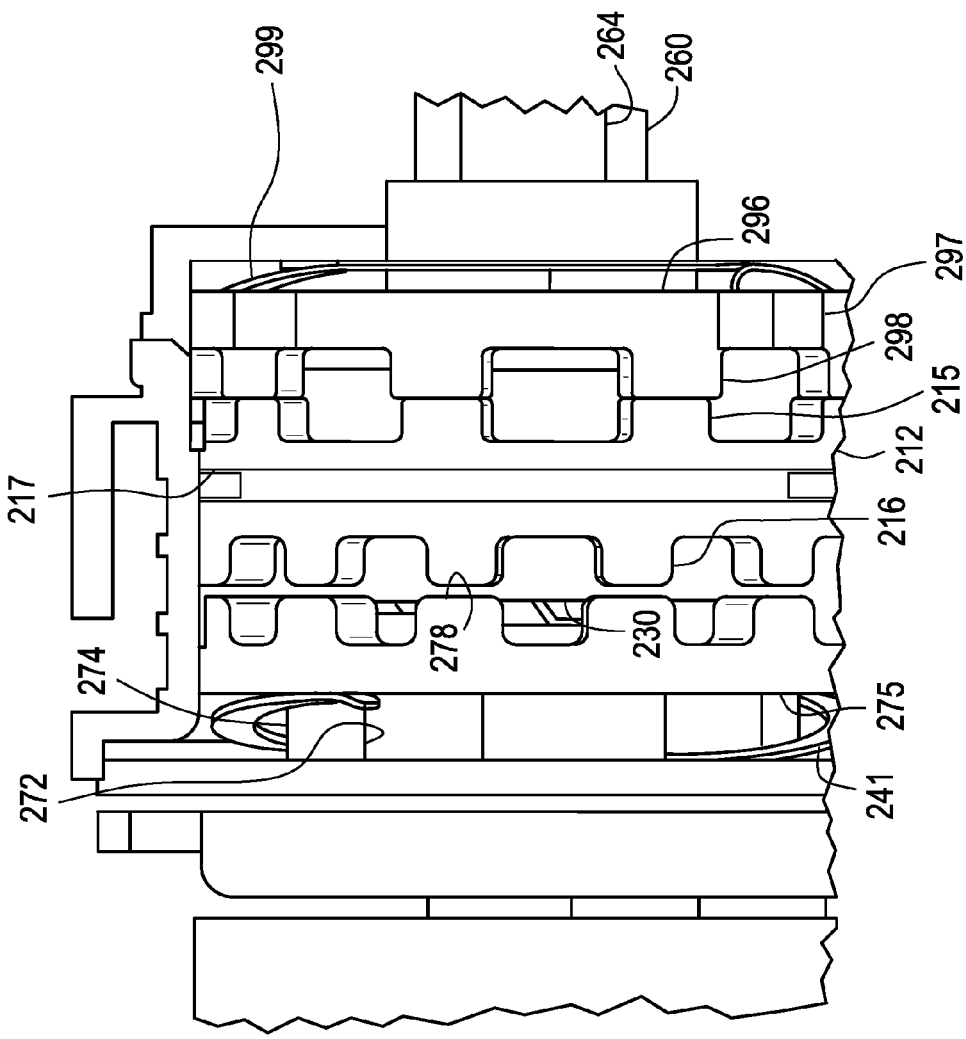

However, as shown in FIG. 17, the angular position of the shift ring 212 (relative to the lock ring 296) may be such that the lugs 215, 298 hit in a head-to-head fashion. In this condition, the shift ring 212 may drive the lock ring 296 in an axial forward direction and against the influence of the spring 299. The radial inward facing grooves (not shown) of the driver housing may guide the axial travel of the lock ring 296 (via the tabs 297). In this way, the shift ring 212 may be located in the desired forward axial position, notwithstanding the head-to-head collision of the lugs 215, 298. Thus, the lock ring 296 may offer a "compliant grounding" feature to the extent that the lock ring 296 may give way to the forward axial travel of the shift ring 212.

In the condition shown in FIG. 17, the shift ring 212 is not yet rotationally grounded to the lock ring 296 (and thus the driver housing). Thus, the shift ring 212 and the output coupling 220 may be rotatable relative to the driver housing.

A user may then power up the driver to actuate the tool chuck. The disk 274 may rotationally drive the PTO drive disk 230 via the cooperating clutch features 279, 236 respectively provided on the confronting surfaces of the disk 274 and the PTO drive disk 230. The PTO drive disk 230 may rotationally drive the chuck actuating shaft 264. Due to frictional drag (e.g., between the cooperating threads of the chuck actuating shaft 264 and the chuck actuating screw), the chuck actuating shaft 264 may rotate together with the input shaft 260 (and thus the output coupling 220 and the shift ring 212). The shift ring 212 may rotate relative to the lock ring 296 until the shift ring 212 is properly clocked to (or angularly positioned relative to) the lock ring 296, as shown in FIG. 18.

Figure 18:
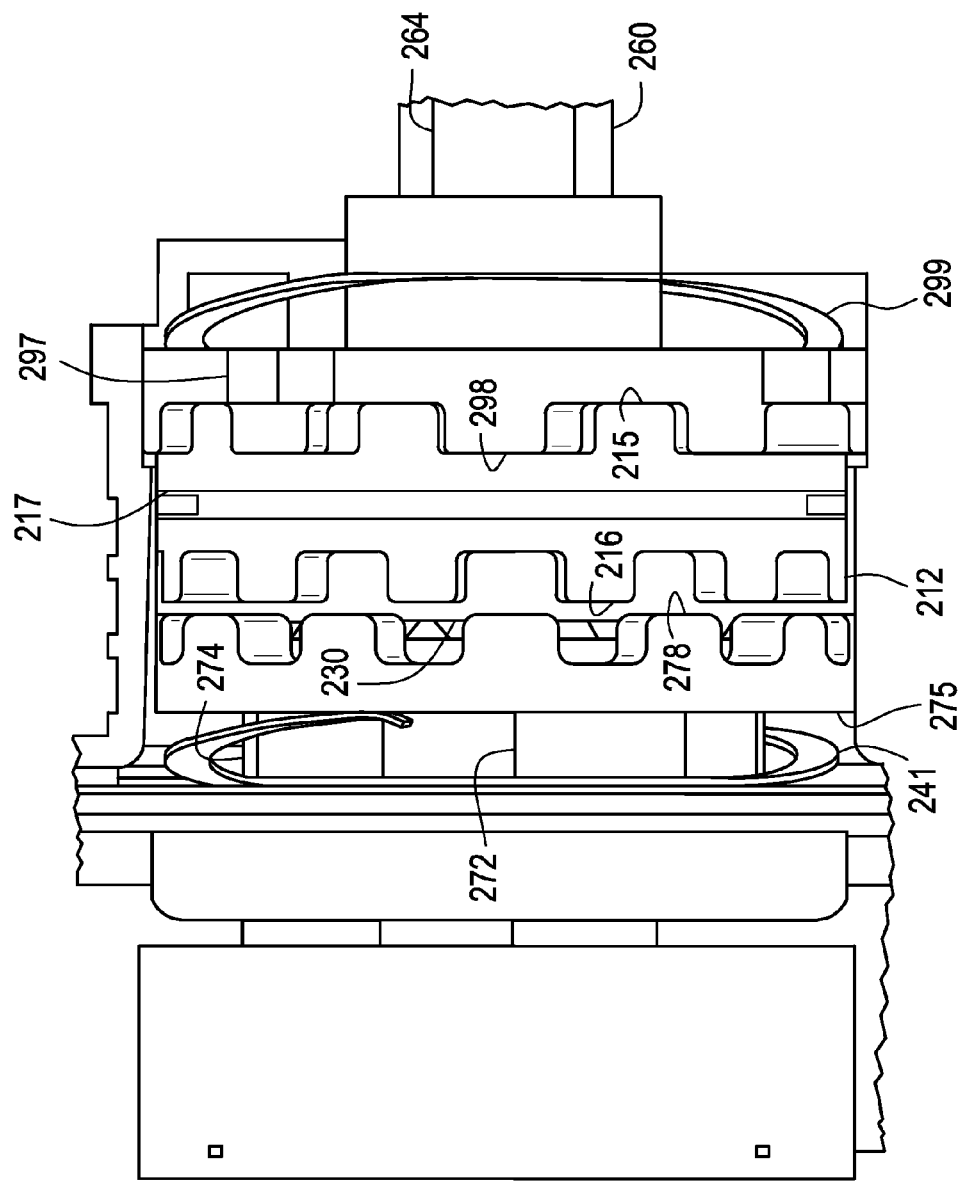

With reference to FIG. 18, the lugs 215 of the shift ring 212 may become aligned with the spaces between the lugs 298 of the lock ring 296. At this time, the springs 299 may influence the lock ring 296 in an axial rearward direction causing the lugs 215 to enter into the spaces between the lugs 298. In this condition, the shift ring 212 and the output coupling 220 (and therefore the input shaft 260 and the chuck actuating screw) may be rotationally grounded to the driver housing.

The disk 274 may continue to rotationally drive the PTO drive disk 230, which in turn may continue to rotationally drive the chuck actuating shaft 264. Here, the chuck actuating shaft 264 may rotate relative to the chuck actuating screw, which may remain rotationally grounded to the driver housing (via the chuck jaws, the input shaft 260, the output coupling 220, the shift ring 212 and the lock ring 296). This relative rotation may cause the chuck actuating screw to advance or retract in the axial direction (depending on the rotation direction of the chuck actuating shaft 264) to open or close the chuck jaws.

During chuck actuation, the input shaft 260, the chuck jaws and the chuck actuating screw may remain rotationally grounded to the driver housing, while the chuck actuating screw may move axially (via the rotational movements of the chuck actuating shaft 264) relative to the input shaft 260 to open and close the chuck jaws. This may be referred to as a dead spindle feature since the user may not be exposed to (or observe) any rotating parts.

Once the tool chuck is tight (i.e., when the chuck jaws clamp the accessory) or fully opened, the cooperating clutch features 279, 236 respectively provided on the confronting surfaces of the disk 274 and the PTO drive disk 230 may give way and slip relative to each other. At this time, the PTO drive disk 230 may move in an axial forward direction against the influence of a spring (not shown). When the cooperating clutch features 279, 236 slip, they may produce an audible indication that the chuck actuation process is complete.

What is claimed is:

1. A power driver comprising:
  a housing;
  a lock member mounted for axial movement on the housing, the lock member being rotationally fixed to the housing;
  a tool chuck mounted for rotation on the housing, the tool chuck supporting jaws;
  a shift member for axial movement relative to the housing and the tool chuck between
    a first position in which the shift member is rotatable relative to the lock member to achieve a DRILL/DRIVE MODE to rotationally drive the jaws, and
    a second position in which the shift member rotationally locks with the lock member if the shift member is meshed with the lock member to achieve a CHUCK MODE to open or close the jaws;
  wherein the lock member is axially displaced by the shift member when the shift member is moved to the second position and the shift member is not meshed with the lock member.

2. The power driver as set forth in claim 1, comprising:
a spring captured between the lock member and the housing to influence the lock member toward the shift member.

3. The power driver as set forth in claim 1, wherein the lock member is ring shaped.

4. The power driver as set forth in claim 1, wherein the lock member has lugs facing the shift member, and
wherein the shift member has lugs to engage with the lugs of the lock member.

5. The power driver as set forth in claim 1, wherein the lock member has axial extended legs that are slidably received by the housing.

6. The power driver as set forth in claim 1, wherein the lock member has radial extended tabs that are slidably received by the housing.

7. The power driver as set forth in claim 1, wherein the shift member is axially moveable to a third position in which the shift member is rotatable relative to the lock member to achieve a MANUAL OVERRIDE MODE to open or close the jaws.

8. The power driver as set forth in claim 1, comprising:
a shift collar mounted for rotation on the housing to influence the shift member into the first and the second positions;
wherein, when the shift member is in the second position, the lock member is axially displaceable by the shift collar to achieve a MANUAL OVERRIDE MODE to open or close the jaws.

9. The power drive as set forth in claim 1, wherein the jaws are threadless jaws.

10. A power driver comprising:
a housing;
a lock member mounted for axial movement on the housing, the lock member being rotationally fixed to the housing;
a tool chuck having
an input shaft, and
a chuck actuating shaft mounted for rotation on the input shaft; and
a power take off mechanism connected to the tool chuck, the power take off mechanism including a shift member for axial movement between
a first position in which the shift member is rotatable relative to the lock member to achieve a DRILL/DRIVE MODE to rotationally drive the input shaft and the chuck actuating shaft together as a unit, and
a second position in which the shift member rotationally locks with the lock member if the shift member is meshed with the lock member to achieve a CHUCK MODE to rotationally drive the chuck actuating shaft relative to the input shaft;
wherein the lock member is axially displaced by the shift member when the shift member is moved to the second position and the shift member is not meshed with the lock member.

11. The power driver as set forth in claim 10, comprising:
a spring captured between the lock member and the housing to influence the lock member toward the shift member.

12. The power driver as set forth in claim 10, wherein the lock member has lugs facing the shift member, and
wherein the shift member has lugs to engage with the lugs of the lock member.

13. The power driver as set forth in claim 10, wherein the lock member has axial extended legs that are slidably received by the housing.

14. The power driver as set forth in claim 10, wherein the lock member has radial extended tabs that are slidably received by the housing.

15. The power driver as set forth in claim 10, wherein the shift member is axially moveable to a third position in which the shift member is rotatable relative to the lock member to achieve a MANUAL OVERRIDE MODE to rotationally drive the input shaft relative to the chuck actuating shaft.

16. The power driver as set forth in claim 10, comprising:
a shift collar mounted for rotation on the housing to influence the shift member into the first and the second positions;
wherein, when the shift member is in the second position, the lock member is axially displaceable by the shift collar to achieve a MANUAL OVERRIDE MODE to rotationally drive the input shaft relative to the chuck actuating shaft.

17. A power driver comprising:
a housing;
a lock member mounted for axial movement on the housing, the lock member being rotationally fixed to the housing;
a transmission output;
a tool chuck having
an input shaft mounted for rotation on the housing and supporting jaws, and
a chuck actuating shaft mounted for rotation on the input shaft;
an output coupling rotationally fixed to the input shaft;
a power take off drive disk rotationally fixed to the chuck actuating shaft;
a shift member mounted for axial movement between
a first position in which the shift member rotationally locks the output coupling to the transmission output, and
a second position in which the shift member rotationally locks the output coupling to the lock member if the shift member is meshed with the lock member;
wherein the lock member is axially displaced by the shift member when the shift member is moved to the second position and the shift member is not meshed with the lock member.

18. The power driver as set forth in claim 17, comprising:
a drive member mounted for axial movement on the transmission output, the drive member being rotationally fixed to the transmission output;
wherein the drive member is axially displaced by the shift member when the shift member is moved to the first position and the shift member is not meshed with the drive member.

19. The power driver as set forth in claim 18, comprising:
a spring captured between the drive member and the housing to influence the drive member toward the shift member.

20. The power driver as set forth in claim 18, wherein the drive member has lugs facing the shift member, and
wherein the shift member has lugs to engage with the lugs of the drive member.

* * * * *